US009526703B2

(12) United States Patent
Vranderick et al.

(10) Patent No.: US 9,526,703 B2
(45) Date of Patent: *Dec. 27, 2016

(54) PLURIMODAL RELEASE FORMULATION OF DOXYLAMINE AND PYRIDOXINE AND/OR METABOLITES OR SALTS THEREOF

(71) Applicant: Duchesnay Inc., Blainville (CA)

(72) Inventors: Manon Vranderick, St-Lazare (CA); Jean-Luc St-Onge, Mirabel (CA); Michele Gallo, Blainville (CA); Éric Gervais, Blainville (CA)

(73) Assignee: Duchesnay Inc., Blainville (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/839,859

(22) Filed: Aug. 28, 2015

(65) Prior Publication Data

US 2016/0058709 A1    Mar. 3, 2016

Related U.S. Application Data

(60) Provisional application No. 62/043,729, filed on Aug. 29, 2014.

(30) Foreign Application Priority Data

Aug. 29, 2014    (WO) ................. PCT/CA2014/050828

(51) Int. Cl.
| | | |
|---|---|---|
| *A61K 9/42* | (2006.01) | |
| *A61K 9/24* | (2006.01) | |
| *A61K 31/4415* | (2006.01) | |
| *A61K 9/20* | (2006.01) | |
| *A61K 31/4402* | (2006.01) | |
| *A61K 9/28* | (2006.01) | |
| *A61K 31/00* | (2006.01) | |

(52) U.S. Cl.
CPC ............ *A61K 9/209* (2013.01); *A61K 9/2027* (2013.01); *A61K 9/2846* (2013.01); *A61K 9/2866* (2013.01); *A61K 31/00* (2013.01); *A61K 31/4402* (2013.01); *A61K 31/4415* (2013.01)

(58) Field of Classification Search
CPC .... A61K 9/2846; A61K 9/2866; A61K 9/209; A61K 31/00; A61K 9/2027; A61K 31/4402; A61K 31/4415
See application file for complete search history.

(56) References Cited

U.S. PATENT DOCUMENTS

| | | | |
|---|---|---|---|
| 4,842,867 A | 6/1989 | Ayer et al. | |
| 6,197,329 B1 | 3/2001 | Hermelin et al. | |
| 6,340,695 B1 * | 1/2002 | Gervais | A61K 9/2009 |
| | | | 514/345 |
| 6,372,255 B1 * | 4/2002 | Saslawski | A61K 31/519 |
| | | | 424/468 |
| 6,924,273 B2 | 8/2005 | Pierce | |
| 7,704,542 B2 | 4/2010 | Bydlon et al. | |
| 2007/0141147 A1 | 6/2007 | Heil et al. | |
| 2015/0025032 A1 | 1/2015 | Vranderick et al. | |
| 2015/0025033 A1 | 1/2015 | Vranderick et al. | |

FOREIGN PATENT DOCUMENTS

| | | |
|---|---|---|
| CA | 2 316 277 A1 | 7/1999 |
| CA | 2 350 195 A1 | 8/2001 |
| JP | 2002-543106 | 12/2002 |
| JP | 2004-521146 | 7/2004 |
| JP | 2008-543723 | 12/2008 |
| WO | WO 0066082 | 11/2000 |
| WO | WO 03/000263 A1 | 1/2003 |
| WO | WO 2006/017341 A2 | 2/2006 |
| WO | WO 2006/087116 | 8/2006 |
| WO | WO 2011/111818 | 9/2011 |
| WO | WO 2011/124953 | 10/2011 |
| WO | WO 2011/163206 | 12/2011 |
| WO | WO 2013/123569 A1 | 8/2013 |

OTHER PUBLICATIONS

Ashkenazi-Hoffnung et al., "Evaluation of the Efficacy and Safety of Bi-Daily Combination Therapy with Pyridoxine and Doxylamine for Nausea and Vomiting of Pregnancy," *IMAJ*, 15(1): 23-26 (2013).

Gill et al., "Systemic Bioavailability and Pharmacokinetics of the Doxylamine—Pyridoxine Delayed-Release Combination (Diclectin)," *Ther Drug Monit*, 33(1): 115-119 (2011).

Koren et al., "Effectiveness of delayed-release doxylamine and pyridoxine for nausea and vomiting of pregnancy: a randomized placebo controlled trial," *Am J Obstet & Gynecol.*, 203(6): 571.el-7 (2010).

Nulman et al., "Pharmacokinetic comparison of a delayed-release combination of doxylamine succinate and pyridoxine hydrocholoride (Diclectin®) and oral solutions of these drugs in healthy women of childbearing age," *Can J Clin Pharmacol.*, 16(3): e400-e406 (2009).

(Continued)

*Primary Examiner* — Suzanne Ziska
(74) *Attorney, Agent, or Firm* — Finnegan, Henderson, Farabow, Garrett & Dunner, LLP

(57) ABSTRACT

A solid oral dosage form comprising a core comprising a doxylamine component and a pyridoxine component coated with an enteric coating is disclosed. The solid oral dosage form further comprises two active ingredient-containing coatings surrounding the enteric coating, the active ingredient-containing coatings being separated from one another by an intermediate coating, and one of the two active ingredient-containing coatings comprising a doxylamine component and being free of a pyridoxine component, and the other of the two active ingredient-containing coatings comprising a pyridoxine component and being free of doxylamine component. Uses of the solid oral dosage form for the alleviation of the symptoms of nausea and vomiting, for example in the case of nausea and vomiting of pregnancy (NVP), are also disclosed.

30 Claims, No Drawings

(56) References Cited

OTHER PUBLICATIONS

Rowland, "Pharmacokinetics of doxylamine given as Bendectin® in the pregnant monkey and baboon," *Reprod Toxica.*, 3:197-202 (1989).
Slikker Jr et al., "Pharmacokinetics of doxylamine, a component of Bendectin®, in the rhesus monkey," *Reprod Toxicol.*, 3: 187-196 (1989).
Notification of Transmittal of the International Search Report and the Written Opinion of the International Searching Authority, or the Declaration, for PCT International Application No. PCT/CA2012/050103, mailed Oct. 18, 2012.
Notification of Transmittal of the International Search Report and the Written Opinion of the International Searching Authority, or the Declaration, for PCT International Application No. PCT/CA2013/050125, mailed Apr. 25, 2013.
Notification of Transmittal of the International Search Report and the Written Opinion of the International Searching Authority, or the Declaration, for PCT International Application No. PCT/CA2014/050231, mailed Jun. 5, 2014, (14 pages).
Notification of Transmittal of the International Search Report and the Written Opinion of the International Searching Authority, or the Declaration, for PCT International Application No. PCT/CA2014/050828, mailed Dec. 4, 2014, (11 pages).
Examination Report for Israeli Patent Application No. 233644 dated Mar. 2, 2015 (including machine translation) (6 pages).
Patent Examination Report No. 1 for Australian Patent Application No. 2013224598 mailed Mar. 5, 2015 (3 pages).
Notice of Reasons for Rejection for Japanese Patent Application No. 2014-557951 dated Mar. 27, 2015, (6 pages).
Extended European Search Report for European Patent Application No. 13751706.6 mailed Mar. 31, 2015, (7 pages).
Office Action mailed Jun. 12, 2014, in U.S. Appl. No. 14/228,214, (10 pages).
Amendment and Response to Restriction Requirement filed Aug. 11, 2014, in U.S. Appl. No. 14/228,214 (9 pages).
Office Action mailed Sep. 23, 2014, in U.S. Appl. No. 14/228,214, (19 pages).
Reply to Office Action under 37 C.F.R. § 1.111 filed Dec. 23, 2014, in U.S. Appl. No. 14/228,214 (19 pages).
Final Office Action mailed Feb. 12, 2015, in U.S. Appl. No. 14/228,214, (22 pages).
Reply to Final Office Action under 37 C.F.R. § 1.116 filed Apr. 13, 2015, in U.S. Appl. No. 14/228,214, (15 pages).
Office Action mailed Aug. 26, 2015, in U.S. Appl. No. 14/228,214, (22 pages).
Office Action mailed Sep. 5, 2014, in U.S. Appl. No. 14/228,228, (8 pages).
Response to Restriction Requirement filed Nov. 4, 2014, in U.S. Appl. No. 14/228,228 (2 pages).
Office Action mailed Dec. 1, 2014, in U.S. Appl. No. 14/228,228, (10 pages).
Reply to Office Action under 37 C.F.R. § 1.111 filed Feb. 27, 2015, in U.S. Appl. No. 14/228,228 (16 pages).
Office Action mailed Aug. 24, 2015, in U.S. Appl. No. 14/506,387, (20 pages).
Decision of Rejection for Japanese Application No. 2014-557951, mailed Sep. 14, 2015, (4 pages)

* cited by examiner

PLURIMODAL RELEASE FORMULATION OF DOXYLAMINE AND PYRIDOXINE AND/OR METABOLITES OR SALTS THEREOF

CROSS REFERENCE TO RELATED APPLICATIONS

This application claims the benefit of U.S. provisional application Ser. No. 62/043,729 and PCT application No. PCT/CA2014/050828, both filed on Aug. 29, 2014, which are incorporated herein by reference in their entirety.

FIELD OF THE INVENTION

The present invention generally relates to dosage forms and uses and packages thereof, for example for the management of nausea and vomiting, such as for the prevention and/or treatment of nausea and vomiting of pregnancy (NVP).

BACKGROUND OF THE INVENTION

Nausea and vomiting of pregnancy (NVP), also referred to as "morning sickness," is very common. It afflicts 50% to 80% of pregnant women with varying degrees of severity.

Commonly occurring within the first 4 to 16 weeks of pregnancy, approximately 20% of women will continue to experience NVP for a longer period of time. Some women may suffer from NVP until the end of the pregnancy. Nausea and vomiting can have serious adverse effects. If severe enough, NVP can cause dehydration, with associated salt and vitamin imbalances. These and other effects can be harmful to the health of the woman and the well-being of her baby. In its most severe form, NVP may manifest itself as hyperemesis gravidarum, a potentially life threatening condition affecting 0.5% to 2% of pregnancies, which is characterized by protracted vomiting, retching, severe dehydration, and weight loss requiring hospitalization.

The delayed release combination of doxylamine succinate/pyridoxine HCl (10 mg each), marketed in Canada under the trade-name Diclectin® and in the United States under the trade-name Diclegis®, is the only medication approved in Canada and U.S. for the treatment of NVP. Its safety and effectiveness for the treatment of NVP is recognized by the medical community, and its safety throughout pregnancy has been long established.

Nevertheless, there is a need for the development of novel pharmaceutical dosage systems and forms, for example those having an improved pharmacokinetics profile and/or stability, for the prevention and treatment of nausea and vomiting, such as in NVP.

The present description refers to a number of documents, the content of which is herein incorporated by reference in their entirety.

SUMMARY OF THE INVENTION

The present invention relates to the following items 1 to 49:

1. A solid oral dosage form comprising: a core comprising about 5 mg to about 40 mg of doxylamine or a salt thereof and about 5 mg to about 40 mg of pyridoxine or a salt thereof; an enteric coating surrounding said core; a first active ingredient-containing coating surrounding said enteric coating and comprising (i) about 5 mg to about 40 mg of doxylamine or a salt thereof, or (ii) about 5 mg to about 40 mg of pyridoxine or a salt thereof; and a second active ingredient-containing coating surrounding said intermediate coating and comprising (i) about 5 mg to about 40 mg of doxylamine or a salt thereof, or (ii) about 5 mg to about 40 mg of pyridoxine or a salt thereof; wherein if said first active ingredient-containing coating comprises said doxylamine or salt thereof, said second active ingredient-containing coating comprises said pyridoxine or salt thereof, and if said first active ingredient-containing coating comprises said pyridoxine or salt thereof, said second active ingredient-containing coating comprises said doxylamine or salt thereof.

2. The solid oral dosage form of item 1, wherein said core comprises about 10 mg of said doxylamine or salt thereof.

3. The solid oral dosage form of item 1 or 2, wherein said core comprises doxylamine succinate.

4. The solid oral dosage form of any one of items 1 to 3, wherein said core comprises about 10 mg of said pyridoxine or salt thereof.

5. The solid oral dosage form of any one of items 1 to 4, wherein said core comprises pyridoxine hydrochloride.

6. The solid oral dosage form of any one of items 1 to 5, wherein said first or second active ingredient-containing coating comprises about 10 mg of said doxylamine or salt thereof.

7. The solid oral dosage form of any one of items 1 to 6, wherein said first or second active ingredient-containing coating comprises doxylamine succinate.

8. The solid oral dosage form of any one of items 1 to 7, wherein said first or second active ingredient-containing coating comprises about 10 mg of said pyridoxine or salt thereof.

9. The solid oral dosage form of any one of items 1 to 8, wherein said first or second active ingredient-containing coating comprises pyridoxine hydrochloride.

10. The solid oral dosage form of any one of items 1 to 9, wherein said first and/or second active ingredient-containing coating comprises a film coating system 11. The solid oral dosage form of item 10, wherein said film coating system comprises a polymer and a plasticizer.

12. The solid oral dosage form of any one of items 1 to 11, wherein said core is present in an amount of about 50% to about 70% (w/w) of said solid oral dosage form.

13. The solid oral dosage form of item 12, wherein said core is present in an amount of about 55% to about 65% (w/w) of said solid oral dosage form.

14. The solid oral dosage form of any one of items 1 to 13, wherein said enteric coating is present in an amount of about 2% to about 15% (w/w) of said solid oral dosage form.

15. The solid oral dosage form of item 14, wherein said enteric coating is present in an amount of about 4% to about 12% (w/w) of said solid oral dosage form.

16. The solid oral dosage form of any one of items 1 to 15, wherein said enteric coating comprises an acrylic polymer or co-polymer.

17. The solid oral dosage form of item 16, wherein said acrylic polymer or co-polymer is a copolymer based on methacrylic acid and ethyl acrylate.

18. The solid oral dosage form of any one of items 1 to 17, wherein said first active ingredient-containing coating is present in an amount of about 4% to about 12% (w/w) in said solid oral dosage form.

19. The solid oral dosage form of item 18, wherein said first active ingredient-containing coating is present in an amount of about 6% to about 10% (w/w) in said solid oral dosage form.

20. The solid oral dosage form of any one of items 1 to 19, further comprising a first intermediate coating surrounding said first active ingredient-containing coating.

21. The solid oral dosage form of item 20, wherein said first intermediate coating is present in an amount of about 1% to about 4% (w/w) in said solid oral dosage form.

22. The solid oral dosage form of item 21, wherein said first intermediate coating is present in an amount of about 2% to about 3% (w/w) in said solid oral dosage form.

23. The solid oral dosage form of any one of items 20 to 22, wherein said first intermediate coating comprises a film coating system.

24. The solid oral dosage form of item 23, wherein said film coating system comprises a polymer and a plasticizer.

25. The solid oral dosage form of any one of items 1 to 24, wherein said second active ingredient-containing coating is present in an amount of about 5% to about 15% (w/w) of said solid oral dosage form.

26. The solid oral dosage form of item 25, wherein said second active ingredient. containing coating is present in an amount of about 8% to about 12% (w/w) of said solid oral dosage form.

27. The solid oral dosage form of any one of items 1 to 26, further comprising a second intermediate coating between said core and said enteric coating.

28. The solid oral dosage form of item 27, wherein said second intermediate coating is present in an amount of about 1% to about 8% (w/w) of said solid oral dosage form.

29. The solid oral dosage form of item 28, wherein said second intermediate coating is present in an amount of about 2% to about 6% (w/w) of said solid oral dosage form.

30. The solid oral dosage form of any one of items 24 to 26, wherein said second intermediate coating comprises a film coating system comprising a polymer and a plasticizer.

31. The solid oral dosage form of any one of items 27 to 30, further comprising a seal coating surrounding said second active ingredient-containing coating.

32. The solid oral dosage form of item 31, wherein said seal coating is present in an amount of about 2% to about 10% (w/w) of said solid oral dosage form.

33. The solid oral dosage form of item 32, wherein said seal coating is present in an amount of about 4% to about 8% (w/w) of said solid oral dosage form.

34. The solid oral dosage form of any one of items 31 to 33, wherein said seal coating comprises a film coating system.

35. The solid oral dosage form of item 34, wherein said film coating system comprises a polymer and a plasticizer.

36. The solid oral dosage form of any one of items 31 to 35, further comprising a solid oral dosage form-coating agent surrounding said seal coating.

37. The solid oral dosage form of item 36, wherein said solid oral dosage form-coating agent is present in an amount of about 0.005% to about 0.5% (w/w) of said solid oral dosage form.

38. The solid oral dosage form of item 36 or 37, wherein said solid oral dosage form-coating agent comprises wax.

39. The solid oral dosage form of any one of items 1 to 38, wherein said core further comprises one or more pharmaceutically acceptable excipients.

40. The solid oral dosage form of item 39, wherein said core comprises microcrystalline cellulose, colloidal silicon dioxide, magnesium trisilicate, croscarmellose sodium and magnesium stearate.

41. The solid oral dosage form of item 40, wherein said core comprises about 60% to about 65% (w/w) of microcrystalline cellulose, about 0.5 to about 1% (w/w) of colloidal silicon dioxide, about 16% to about 20% (w/w) of magnesium trisilicate, about 2% to about 3% (w/w) of croscarmellose sodium, and about 2% to about 3% (w/w) of magnesium stearate.

42. The solid oral dosage form of any one of items 1 to 41, wherein said solid oral dosage form is a tablet.

43. The solid oral dosage form of any one of items 1 to 42, for use in alleviating the symptoms of nausea and vomiting of human pregnancy.

44. The solid oral dosage form of any one of items 1 to 42, for use in the manufacture of a medicament for alleviating the symptoms of nausea and vomiting of human pregnancy.

45. Use of the solid oral dosage form of any one of items 1 to 42, for alleviating the symptoms of nausea and vomiting of human pregnancy.

46. Use of the solid oral dosage form of any one of items 1 to 42, for the manufacture of a medicament for alleviating the symptoms of nausea and vomiting of human pregnancy.

47. A method for alleviating the symptoms of nausea and vomiting of human pregnancy, said method comprising administering the solid oral dosage form of any one of items 1 to 42 to a pregnant human female in need thereof.

48. A package comprising the solid oral dosage form of any one of items 1 to 42.

49. The package of item 48, further comprising instructions for use of said solid oral dosage form for alleviating the symptoms of nausea and vomiting of human pregnancy.

The present invention also relates to the following items 1a to 30a:

1a. A solid oral dosage form comprising: (a) a core comprising from about 5 mg to about 40 mg of doxylamine and/or a pharmaceutically acceptable salt thereof and from about 5 mg to about 40 mg of pyridoxine and/or a pharmaceutically acceptable salt thereof; (b) an enteric coating surrounding said core; (c) a first active ingredient-containing coating surrounding said enteric coating and comprising (i) from about 5 mg to about 40 mg of doxylamine and/or a pharmaceutically acceptable salt thereof, or (ii) from about 5 mg to about 40 mg of pyridoxine and/or a pharmaceutically acceptable salt thereof; and (d) a second active ingredient-containing coating surrounding said first active ingredient-containing coating and comprising (i) from about 5 mg to about 40 mg of doxylamine and/or a pharmaceutically acceptable salt thereof, or (ii) from about 5 mg to about 40 mg of pyridoxine and/or a pharmaceutically acceptable salt thereof; wherein if said first active ingredient-containing coating comprises said doxylamine and/or pharmaceutically acceptable salt thereof, said second active ingredient-containing coating comprises said pyridoxine and/or pharmaceutically acceptable salt thereof, and if said first active ingredient-containing coating comprises said pyridoxine and/or pharmaceutically acceptable salt thereof, said second active ingredient-containing coating comprises said doxylamine and/or pharmaceutically acceptable salt thereof.

2a. The solid oral dosage form of item 1a, wherein said core comprises about 10 mg of said doxylamine or pharmaceutically acceptable salt thereof.

3a. The solid oral dosage form of item 1a, wherein said core comprises doxylamine succinate.

4a. The solid oral dosage form of item 1a, wherein said core comprises about 10 mg of said pyridoxine or pharmaceutically acceptable salt thereof.

5a. The solid oral dosage form of item 1a, wherein said core comprises pyridoxine hydrochloride.

6a. The solid oral dosage form of item 1a, wherein said first or second active ingredient-containing coating comprises about 10 mg of said doxylamine or pharmaceutically acceptable salt thereof.

7a. The solid oral dosage form of item 1a, wherein said first or second active ingredient-containing coating comprises doxylamine succinate.

8a. The solid oral dosage form of item 1a, wherein said first or second active ingredient-containing coating comprises about 10 mg of said pyridoxine or pharmaceutically acceptable salt thereof.

9a. The solid oral dosage form of item 1a, wherein said first or second active ingredient-containing coating comprises pyridoxine hydrochloride.

10a. The solid oral dosage form of item 1a, wherein said first and/or second active ingredient-containing coating comprises a film coating system.

11a. The solid oral dosage form of item 1a, wherein said core is present in an amount of about 50% to about 70% (w/w) of said solid oral dosage form.

12a. The solid oral dosage form of item 1a, wherein said enteric coating is present in an amount of about 2% to about 15% (w/w) of said solid oral dosage form.

13a. The solid oral dosage form of item 1a, wherein said enteric coating comprises an acrylic polymer or co-polymer.

14a. The solid oral dosage form of item 13a, wherein said acrylic polymer or co-polymer is a copolymer based on methacrylic acid and ethyl acrylate.

15a. The solid oral dosage form of item 1a, wherein said first active ingredient-containing coating is present in an amount of about 4% to about 12% (w/w) in said solid oral dosage form.

16a. The solid oral dosage form of item 1a, further comprising a first intermediate coating surrounding said first active ingredient-containing coating.

17a. The solid oral dosage form of item 16a, wherein said first intermediate coating is present in an amount of about 1% to about 4% (w/w) in said solid oral dosage form.

18a. The solid oral dosage form of item 16a, wherein said first intermediate coating comprises a film coating system.

19a. The solid oral dosage form of item 1a, wherein said second active ingredient-containing coating is present in an amount of about 5% to about 15% (w/w) of said solid oral dosage form.

20a. The solid oral dosage form of item 1a, further comprising a second intermediate coating between said core and said enteric coating.

21a. The solid oral dosage form of item 1a, further comprising a third intermediate coating between said enteric coating and said first active ingredient-containing coating.

22a. The solid oral dosage form of item 1a, further comprising a seal coating surrounding said second active ingredient-containing coating.

23a. The solid oral dosage form of item 22a, wherein said seal coating is present in an amount of about 2% to about 10% (w/w) of said solid oral dosage form.

24a. The solid oral dosage form of item 22a, wherein said seal coating comprises a film coating system.

25a. The solid oral dosage form of item 22a, further comprising a solid oral dosage form-coating agent surrounding said seal coating.

26a. The solid oral dosage form of item 25a, wherein said solid oral dosage form-coating agent is present in an amount of about 0.005% to about 0.5% (w/w) of said solid oral dosage form.

27a. The solid oral dosage form of item 25a, wherein said solid oral dosage form-coating agent comprises wax.

28a. The solid oral dosage form of item 1a, wherein said solid oral dosage form is a tablet.

29a. A solid oral dosage form comprising: (a) a core comprising about 10 mg of doxylamine succinate and about 10 mg of pyridoxine hydrochloride; (b) an enteric coating surrounding said core; (c) a first active ingredient-containing coating surrounding said enteric coating and comprising about 10 mg of pyridoxine hydrochloride; (d) a second active ingredient-containing coating surrounding said first active ingredient-containing coating and comprising about 10 mg of doxylamine succinate; (e) a seal coating surrounding said second active ingredient-containing coating; (f) a solid oral dosage form-coating agent surrounding said seal coating; (g) a first intermediate coating between said first active ingredient-containing coating and said second active ingredient-containing coating; (h) a second intermediate coating between said core and said enteric coating; and (i) a third intermediate coating between said enteric coating and said first active ingredient-containing coating.

30a. A method for alleviating the symptoms of nausea and vomiting of human pregnancy, said method comprising administering the solid oral dosage form of item 1a to a pregnant human female in need thereof.

Other objects, advantages and features of the present invention will become more apparent upon reading of the following non-restrictive description of specific embodiments thereof, given by way of example only with reference to the accompanying drawings.

DESCRIPTION OF ILLUSTRATIVE EMBODIMENTS

The studies described herein show an improvement in the degradation product profile of doxylamine succinate and pyridoxine HCl in the immediate release component of plurimodal release formulations when the two ingredients are incorporated into separate coatings.

Accordingly, in a first aspect, the present invention provides a solid oral dosage form comprising: a core comprising a doxylamine component and a pyridoxine component; an enteric coating surrounding said core; a first active ingredient-containing coating surrounding said enteric coating and comprising a doxylamine component or a pyridoxine component; and a second active ingredient-containing coating surrounding said intermediate coating and comprising a doxylamine component or a pyridoxine component; wherein if said first active ingredient-containing coating comprises said doxylamine component, said second active ingredient-containing coating comprises said pyridoxine component, and if said first active ingredient-containing coating comprises said pyridoxine component, said second active ingredient-containing coating comprises said doxylamine component.

In another aspect, the present invention provides a solid oral dosage form comprising: a core comprising about 5 mg to about 40 mg of doxylamine or a salt thereof and about 5 mg to about 40 mg of pyridoxine or a salt thereof; an enteric coating surrounding said core; an first active ingredient-containing coating surrounding said enteric coating and comprising (i) about 5 mg to about 40 mg of doxylamine or a salt thereof, or (ii) about 5 mg to about 40 mg of pyridoxine or a salt thereof; and a second active ingredient-containing coating surrounding said intermediate coating and comprising (i) about 5 mg to about 40 mg of doxylamine or a salt thereof, or (ii) about 5 mg to about 40 mg of pyridoxine or a salt thereof; wherein if said first active ingredient-containing coating comprises said doxylamine or salt thereof, said second active ingredient-containing coating comprises said pyridoxine or salt thereof, and if said first active ingredient-containing coating comprises said pyridoxine or salt thereof, said second active ingredient-containing coating comprises said doxylamine or salt thereof.

In another aspect, the present invention provides a solid oral dosage form (e.g., a pharmaceutical tablet) comprising a core coated with an enteric coating, the core comprising a doxylamine component (doxylamine or a salt thereof such as doxylamine succinate) and a pyridoxine component (pyridoxine or a salt thereof such as pyridoxine hydrochloride), the core coated with the enteric coating being further coated with two active ingredient-containing coatings located on top of (i.e. surrounding/covering) the enteric coating, one of the two active ingredient-containing coatings comprising a doxylamine component (doxylamine or a salt thereof such as doxylamine succinate) and being substantially free of a pyridoxine component (pyridoxine or a salt thereof such as pyridoxine hydrochloride), and the other of the two active ingredient-containing coatings comprising a pyridoxine component (pyridoxine or a salt thereof such as pyridoxine hydrochloride) and being substantially free of a doxylamine component (doxylamine or a salt thereof such as doxylamine succinate). In an embodiment, the two active ingredient-containing coatings are separated from one another by an intermediate coating.

The term "about" is used herein to indicate that a value includes an inherent variation of error for the device or the method being employed to determine the value, or encompass values close to the recited values, for example within 10% of the recited values (or range of values).

The term "core" as used herein refers to the central component of the solid oral dosage form that comprises active ingredient(s) and that is coated with the different coatings defined herein. The core may further comprise one or more pharmaceutically acceptable excipients. Further, in embodiments, one or more of the coatings described herein may further comprise one or more pharmaceutically acceptable excipients.

An "excipient," as used herein, has its normal meaning in the art and is any ingredient of an oral dosage form that is not an active ingredient (drug) itself. Excipients include for example binders, lubricants, diluents, fillers, thickening agents, disintegrants, plasticizers, coatings, barrier layer formulations, lubricants, stabilizing agent, release-delaying agents and other components. "Pharmaceutically acceptable excipient" as used herein refers to any excipient that does not interfere with effectiveness of the biological activity of the active ingredients and that is not toxic to the subject, i.e., is a type of excipient and/or is for use in an amount which is not toxic to the subject. In the case of a pregnant human female subject, the pharmaceutically acceptable excipient is also not toxic to the embryo or fetus, i.e., a pharmaceutical excipient suitable for administration to a pregnant female. Thus, in dosage forms for administration to pregnant subjects, pharmaceutically acceptable excipients that have teratogenic properties and/or that are contraindicated for use in pregnancy are excluded. Excipients are well known in the art, and the present system is not limited in these respects. See, for example, Remington's Pharmaceutical Sciences, 18$^{th}$ Edition, A. Gennaro, Ed., Mack Pub. Co. (Easton, Pa 1990), Chapters 88-91. In certain embodiments, one or more formulations of the dosage form include excipients, including for example and without limitation, one or more binders (binding agents), thickening agents, surfactants, diluents, release-delaying agents, colorants, flavoring agents, fillers, disintegrants/dissolution promoting agents, lubricants, plasticizers, silica flow conditioners, glidants, anti-caking agents, anti-tacking agents, stabilizing agents, anti-static agents, swelling agents and any combinations thereof. As those of skill would recognize, a single excipient can fulfill more than two functions at once, e.g., can act as both a binding agent and a thickening agent. As those of skill will also recognize, these terms are not necessarily mutually exclusive.

Useful diluents, e.g., fillers, employable in the core and/or a coating of the solid oral dosage form may include, for example and without limitation, dicalcium phosphate, calcium diphosphate, calcium carbonate, calcium sulfate, lactose, cellulose, kaolin, sodium chloride, starches, powdered sugar, colloidal silicon dioxide, titanium oxide, alumina, talc, colloidal silica, microcrystalline cellulose, silicified micro crystalline cellulose and combinations thereof. Fillers that can add bulk to tablets with minimal drug dosage to produce tablets of adequate size and weight include croscarmellose sodium NF/EP (e.g., Ac-Di-Sol); anhydrous lactose NF/EP (e.g., Pharmatose™ DCL 21); and/or povidone USP/EP. In an embodiment, the core of the solid oral dosage form comprises a diluent or filler, preferably microcrystalline cellulose.

Binder materials employable in the core and/or a coating of the solid oral dosage form may include, for example and without limitation, starches (including corn starch and pregelatinized starch), gelatin, sugars (including sucrose, glucose, dextrose and lactose), polyethylene glycol, povidone, waxes, and natural and synthetic gums, e.g., acacia sodium alginate, polyvinylpyrrolidone, cellulosic polymers (e.g., hydroxypropyl cellulose, hydroxypropyl methylcellulose, methyl cellulose, hydroxyethyl cellulose, carboxymethylcellulose, colloidal silicon dioxide NREP (e.g., Cab-O-Sil™ M5P), Silicified Microcrystalline Cellulose (SMCC), e.g., Silicified microcrystalline cellulose NF/EP (e.g., Prosolv™ SMCC 90), and silicon dioxide, mixtures thereof, and the like), veegum, and combinations thereof, Useful lubricants employable in the core and/or a coating of the solid oral dosage form may include, for example, canola oil, glyceryl palmitostearate, hydrogenated vegetable oil (type I), magnesium oxide, magnesium stearate, mineral oil, poloxamer, polyethylene glycol, sodium lauryl sulfate, sodium stearate fumarate, stearic acid, talc and, zinc stearate, glyceryl behapate, magnesium lauryl sulfate, boric acid, sodium benzoate, sodium acetate, sodium benzoate/sodium acetate (in combination), DL leucine, calcium stearate, sodium stearyl fumarate, mixtures thereof, and the like. In an embodiment, the core of the solid oral dosage form comprises a lubricant, preferably magnesium stearate.

Bulking agents employable in the core and/or a coating of the solid oral dosage form may include, for example: microcrystalline cellulose, for example, AVICEL® (FMC Corp.) or EMCOCEL® (Mendell Inc.), which also has binder properties; dicalcium phosphate, for example, EMCOMPRESS (Mendell Inc.); calcium sulfate, for example, COMPACTROL (Mendell Inc.); and starches, for example, Starch 1500; and polyethylene glycols (CARBOWAX®).

Suitable disintegrating or dissolution promoting agents employable in the core and/or a coating of the solid oral dosage form may include, but are not limited to: starches, clays, celluloses, alginates, gums, crosslinked polymers, colloidal silicon dioxide, osmogens, mixtures thereof, and the like, such as crosslinked sodium carboxymethyl cellulose (AC-DI-SOL®), sodium croscarmelose, sodium starch glycolate (EXPLOTAB®, PRIMO JEL®) crosslinked polyvinylpolypyrrolidone (PLASONE-XL®), sodium chloride, sucrose, lactose and mannitol. In an embodiment, the core of the solid oral dosage form comprises a disintegrating agent, preferably sodium croscarmelose.

Antiadherents and glidants employable in the core and/or a coating of the solid oral dosage form may include talc, starches (e.g., cornstarch), celluloses, silicon dioxide, sodium lauryl sulfate, colloidal silica dioxide, and metallic stearates, among others.

Examples of silica flow conditioners include colloidal silicon dioxide, magnesium aluminum silicate and guar gum. In an embodiment, the core of the solid oral dosage form comprises a silica flow conditioner, preferably silicon dioxide.

Suitable surfactants employable in the core and/or a coating of the solid oral dosage form include pharmaceutically acceptable non-ionic, ionic and anionic surfactants. An example of a surfactant is sodium lauryl sulfate. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. If desired, flavoring, coloring and/or sweetening agents may be added as well.

Examples of stabilizing agents employable in the core and/or a coating of the solid oral dosage form include acacia, albumin, polyvinyl alcohol, alginic acid, bentonite, dicalcium phosphate, carboxymethylcellulose, hydroxypropylcellulose, colloidal silicon dioxide, cyclodextrins, glyceryl monostearate, hydroxypropyl methylcellulose, magnesium trisilicate, magnesium aluminum silicate, propylene glycol, propylene glycol alginate, sodium alginate, carnauba wax, xanthan gum, starch, stearate(s), stearic acid, stearic monoglyceride and stearyl alcohol. In an embodiment, core of the solid oral dosage form comprises a stabilizing agent, preferably magnesium trisilicate.

Optionally, a thickening agent can be added to provide the dosage form (e.g., tablet) with an accurately timed disintegration behavior. The dosage form optionally disintegrates at a rate which is sufficiently slow to permit it to be swallowed easily, but fast enough to give an excellent suspension in water within 60 seconds. The thickening agent can be for example talc USP/EP, a natural gum, such as guar gum or gum arabic, or a cellulose derivative such as microcrystalline cellulose NF/EP (e.g., Avicel™ PH 102), methylcellulose, ethylcellulose or hydroxyethylcellulose. A useful thickening agent is hydroxypropyl methylcellulose, an adjuvant which is available in various viscosity grades.

Similarly, suitable plasticizers employable in the core and/or a coating of the solid oral dosage form include: acetylated monoglycerides; these can be used as food additives; Alkyl citrates, used in food packagings, medical products, cosmetics and children toys; Triethyl citrate (TEC); Acetyl triethyl citrate (ATEC), higher boiling point and lower volatility than TEC; Tributyl citrate (TBC); Acetyl tributyl citrate (ATBC), compatible with PVC and vinyl chloride copolymers; Trioctyl citrate (TOC), also used for gums and controlled release medicines; Acetyl trioctyl citrate (ATOC), also used for printing ink; Trihexyl citrate (THC), compatible with PVC, also used for controlled release medicines; Acetyl trihexyl citrate (ATHC), compatible with PVC; Butyryl trihexyl citrate (BTHC, trihexyl o-butyryl citrate), compatible with PVC; Trimethyl citrate (TMC), compatible with PVC; alkyl sulphonic acid phenyl ester, polyethylene glycol (PEG) or any combination thereof. Optionally, the plasticizer can comprise triethyl citrate NF/EP.

In an embodiment, the core comprises one or more fillers, one or more glidants, one or more disintegrants and/or one or more lubricants.

In an embodiment, the core comprises microcrystalline cellulose, colloidal silicon dioxide, magnesium trisilicate, croscarmellose sodium and magnesium stearate. In an embodiment, the microcrystalline cellulose is present in an amount of about 60% to about 65% (w/w) of said core. In an embodiment, the colloidal silicon dioxide is present in an amount of about 0.5 to about 1% (w/w) of said core. In an embodiment, the magnesium trisilicate is present in an amount of about 16% to about 20% (w/w) of said core. In an embodiment, the croscarmellose sodium is present in an amount of about 2% to about 3% (w/w) of said core. In an embodiment, the magnesium stearate is present in an amount of about 2% to about 3% (w/w) of said core.

In a further embodiment, the core comprises about 60% to about 65% (w/w) of microcrystalline cellulose, about 0.5 to about 1% (w/w) of colloidal silicon dioxide, about 16% to about 20% (w/w) of magnesium trisilicate, about 2% to about 3% (w/w) of croscarmellose sodium, and about 2% to about 3% (w/w) of magnesium stearate.

In an embodiment, the core comprises from about 5 mg to about 35 mg of doxylamine or a salt thereof. In another embodiment, the core comprises from about 5 mg to about 30 mg of doxylamine or a salt thereof. In another embodiment, the core comprises from about 5 mg to about 25 mg of doxylamine or a salt thereof. In another embodiment, the core comprises from about 5 mg to about 20 mg of doxylamine or a salt thereof. In another embodiment, the core comprises from about 5 mg to about 15 mg of doxylamine or a salt thereof. In another embodiment, the core comprises from about 5, 6, 7, 8, 9, 10, 11, 12, 13, 14 or 15 mg of doxylamine or a salt thereof.

In an embodiment, the core comprises from about 5 mg to about 35 mg of pyridoxine or a salt thereof. In another embodiment, the core comprises from about 5 mg to about 30 mg of pyridoxine or a salt thereof. In another embodiment, the core comprises from about 5 mg to about 25 mg of pyridoxine or a salt thereof. In another embodiment, the core comprises from about 5 mg to about 20 mg of pyridoxine or a salt thereof. In another embodiment, the core comprises from about 5 mg to about 15 mg of pyridoxine or a salt thereof. In another embodiment, the core comprises from about 5, 6, 7, 8, 9, 10, 11, 12, 13, 14 or 15 mg of pyridoxine or a salt thereof.

In an embodiment, the core is present in the solid oral dosage form in an amount of about 40% to about 80% or about 50% to about 70% (w/w) of the solid oral dosage form, in further embodiments in an amount of about 55% to about 65% (w/w), e.g., 55, 56, 57, 58, 59, 60, 61, 62, 63, 64 or 65%, of the solid oral dosage form. In an embodiment, the total weight of the core is of about 100 mg to about 200 mg, in further embodiments of about 120 mg to about 180 mg, about 130 mg to about 170 mg, or about 140 to 150 mg (e.g., about 145 mg). In an embodiment, the core comprises: about 80 to about 100 mg (e.g., about 90 mg) of microcrystalline cellulose; about 5 to about 15 mg (e.g., about 10 mg) of doxylamine or a salt thereof (e.g., doxylamine succinate); about 5 to about 15 mg (e.g., about 10 mg) of pyridoxine or a salt thereof (e.g., pyridoxine hydrochloride); about 0.5 to about 2 mg (e.g., about 1 mg) of colloidal silicon dioxide; about 20 mg to about 30 mg (e.g., about 26-27 mg) of magnesium trisilicate; about 3 mg to about 4 mg (e.g., about 3.5 or 3.6 mg) of croscarmellose sodium; and about 3.5 mg to about 4.5 mg (e.g., about 4 mg) of magnesium stearate.

The term "coating" as used herein refers to a layer or film, made of one or more suitable materials, that surrounds/covers (and preferably adheres to) an inner component of the solid oral dosage form. The coating may comprise any agent or combination of agents suitable to form a layer or film, such as polymeric materials (e.g., cellulosic-based polymers, acrylic-based polymers, polyvinyl-based polymers. Coating materials/polymers and coating systems comprising polymer(s), plasticizers, pigments, etc. are known in the art. Examples of coating polymers and systems include the OPADRY® series of film coating system (COLORCON®), INSTACOAT® film coating systems (IDEAL CURES® PVT LTD), AQUARIUS™ film coating systems (ASHLAND®), SHEFFCOAT™ film coating systems (KERRY®), SEPIFILM™ film coating systems (SEPPIC®), PlasACRYL™ coating systems (based on EUDRAGIT® polymers) from EVONIK®, KOLLICOAT™ coating systems (BASF®), SPECTRABLEND™ coating systems (SENSIENT®), VIVAPHARM® HPMC (JRS PHARMA®). In an embodiment, the coating comprises an OPADRY® film coating system.

The term "enteric coating" is used to refer to a coating that is made from gastric resistant materials (polymers), i.e. which remain substantially intact in the acidic environment of the stomach, but dissolve readily at the elevated pH of the intestine (and/or in the presence of degradative enzymes that are characteristically present in the intestine). Polymers suitable to form enteric coating are well known in the art and include, for example, cellulosic polymers (e.g., cellulose acetate phthalate, cellulose acetate trimellitate, cellulose acetate succinate polymers, hydroxypropyl cellulose, hydroxyethyl cellulose, hydroxymethyl cellulose, hydroxypropyl methylcellulose phthalate (HPMCP), hydroxypropyl methyl cellulose acetate succinate (hypromellose acetate succinate), carboxymethylcellulose sodium), acrylic acid polymers and copolymers, preferably formed from acrylic acid, methacrylic acid, methyl acrylate, ethyl acrylate, methyl methacrylate and/or ethyl methacrylate (e.g., methacrylate-based polymers/copolymers (e.g., EUDRAGIT® polymers such as EUDRAGIT® L30D-55, L100-55, L-100, EUDRAGIT® S, EUDRAGIT® NE, RL and RS), vinyl polymers and copolymers such as polyvinyl pyrrolidone, vinyl acetate, polyvinyl acetate phthalate, vinylacetate phthalate, vinylacetate crotonic acid copolymer, and ethylene-vinyl acetate copolymer (PVAP), enzymatically degradable polymers such as azo polymers, pectin, chitosan, amylose and guar gum; zein and shellac. Examples of entering coating systems include the OPADRY®, SURETERIC® or Acryl-EZE® Enteric system (COLORCON®), and SHEFFCOAT™ ENT system (KERRY®). Combinations of different enteric materials may also be used. Multi-layer coatings using different polymers may also be applied. The properties, manufacture and design of enteric delivery systems are well known to those of ordinary skill in the art. See, e.g., Development of Biopharmaceutical Parenteral Dosage Forms (Drugs and the Pharmaceutical Sciences), by Bontempo (Publishers: lnforma Healthcare (Jul. 25, 1997).

In an embodiment, the enteric coating comprises an acrylic polymer or co-polymer, in a further embodiment a copolymer based on methacrylic acid and ethyl acrylate (e.g., Poly(methacylic acid-co-ethyl acrylate) 1:1, commercialized under the trade-name EUDRAGIT® L 100-55). In a further embodiment, the enteric coating comprises an Acryl-EZE® enteric coating system. In yet a further embodiment, the enteric coating further comprises an antifoaming agent, for example simethicone or simethicone emulsion (e.g., Simethicone Emulsion 30% USP, KH) and a plasticizer, for example polyethylene glycol (PEG) 8000, triacetin, or triethyl citrate (TEC) (e.g., Triethyl Citrate NF, K). In an embodiment, the weight of the enteric coating in the solid oral dosage form is about 10 to about 20 mg, in further embodiments about 14 to about 18 mg, e.g., about 16 mg. In a further embodiment, the enteric coating comprises about 0.001 to about 0.005 mg of antifoaming agent (e.g., simethicone emulsion), about 1 to about 2 mg of plasticizer (e.g., TEC) and about 14 mg to about 15 mg of enteric material/polymer (e.g., Acryl-EZE® enteric coating system).

The enteric coating of the solid oral dosage form described herein allows the delayed release of the active ingredients (doxylamine and pyridoxine components) comprised in the core. In an embodiment, the enteric coating is present in an amount of about 1% to about 20% (w/w) of said solid oral dosage form. In further embodiments, the enteric coating is present in an amount of about 2% to about 15%, about 4% to about 12% or about 4% to about 10%, for example about 4, 5, 6, 7, 8, 9, or 10% (w/w), of said solid oral dosage form. The first active ingredient-containing coating surrounds or envelops the enteric coating and comprises either the doxylamine component (e.g., doxylamine or salt thereof) or the pyridoxine component (e.g., pyridoxine or salt thereof). In an embodiment, the first active ingredient-containing coating comprises the pyridoxine component, e.g., pyridoxine or salt thereof such as pyridoxine HCl.

The first active ingredient-containing coating may further comprise any non-enteric coating material suitable to form a layer or film, as described above. In an embodiment, the first active ingredient-containing coating comprises a film coating system comprising a polymer and a plasticizer, for example an OPADRY® film coating system. The ratio of active ingredient to coating material in the first active ingredient-containing coating may be of about 1:4 to about 4:1, for example of about 1:3 to about 3:1 or about 1:2 to about 2:1, in further embodiments from about 1:1.5 to about 1.5:1, for example about 1:1.

In an embodiment, the first active ingredient-containing coating comprises from about 5 mg to about 35 mg of doxylamine or a salt thereof. In another embodiment, the first active ingredient-containing coating comprises from about 5 mg to about 30 mg of doxylamine or a salt thereof. In another embodiment, the first active ingredient-containing coating comprises from about 5 mg to about 25 mg of doxylamine or a salt thereof. In another embodiment, the first active ingredient-containing coating comprises from about 5 mg to about 20 mg of doxylamine or a salt thereof. In another embodiment, the first active ingredient-containing coating comprises from about 5 mg to about 15 mg of doxylamine or a salt thereof. In another embodiment, the first active ingredient-containing coating comprises from about 5, 6, 7, 8, 9, 10, 11, 12, 13, 14 or 15 mg of doxylamine or a salt thereof.

In an embodiment, the first active ingredient-containing coating comprises from about 5 mg to about 35 mg of pyridoxine or a salt thereof. In another embodiment, the first active ingredient-containing coating comprises from about 5 mg to about 30 mg of pyridoxine or a salt thereof. In another embodiment, the first active ingredient-containing coating comprises from about 5 mg to about 25 mg of pyridoxine or a salt thereof. In another embodiment, the first active ingredient-containing coating comprises from about 5 mg to about 20 mg of pyridoxine or a salt thereof. In another embodiment, the first active ingredient-containing coating comprises from about 5 mg to about 15 mg of pyridoxine or a salt thereof. In another embodiment, the first active ingredient-containing coating comprises from about 5, 6, 7, 8, 9, 10, 11, 12, 13, 14 or 15 mg of pyridoxine or a salt thereof.

In an embodiment, the first active ingredient-containing coating comprises about 8 to 12 mg (e.g., about 10 mg) of pyridoxine or salt thereof such as pyridoxine HCl, and about 8 mg to about 10 mg (e.g., about 9 mg) of coating material (e.g., OPADRY® film coating).

In an embodiment, the first active ingredient-containing coating is present in an amount of about 1% to about 20% (w/w) of said solid oral dosage form. In further embodiments, the first active ingredient-containing coating is present in an amount of about 2% to about 15%, about 2% to about 10%, or about 4% to about 8%, for example about 4, 5, 6, 7 or 8% (w/w), of said solid oral dosage form.

The second active ingredient-containing coating surrounds or envelops the intermediate coating (the first and second active ingredient-containing coatings are separated by the intermediate coating) and comprises either the doxylamine component (e.g., doxylamine or salt thereof) or the pyridoxine component (e.g., pyridoxine or salt thereof), depending on whether the first active ingredient-containing coating the doxylamine component (e.g., doxylamine or salt thereof) or the pyridoxine component (e.g., pyridoxine or salt thereof). In an embodiment, the second active ingredient-containing coating comprises the doxylamine component, e.g., doxylamine or salt thereof such as doxylamine succinate.

The second active ingredient-containing coating may further comprise any non-enteric coating material suitable to form a layer or film, as described above. In an embodiment, the second active ingredient-containing coating comprises a film coating system comprising a polymer and a plasticizer, for example an OPADRY® film coating system. The ratio of active ingredient to coating material in the second active ingredient-containing coating may be of about 1:4 to about 4:1, for example of about 1:3 to about 3:1 or about 1:2 to about 2:1, in further embodiments from about 1:1 to about 1.5:1, for example about 1.4 or 1.5:1.

In an embodiment, the second active ingredient-containing coating comprises from about 5 mg to about 35 mg of doxylamine or a salt thereof. In another embodiment, the second active ingredient-containing coating comprises from about 5 mg to about 30 mg of doxylamine or a salt thereof. In another embodiment, the second active ingredient-containing coating comprises from about 5 mg to about 25 mg of doxylamine or a salt thereof. In another embodiment, the second active ingredient-containing coating comprises from about 5 mg to about 20 mg of doxylamine or a salt thereof. In another embodiment, the second active ingredient-containing coating comprises from about 5 mg to about 15 mg of doxylamine or a salt thereof. In another embodiment, the second active ingredient-containing coating comprises from about 5, 6, 7, 8, 9, 10, 11, 12, 13, 14 or 15 mg of doxylamine or a salt thereof.

In an embodiment, the second active ingredient-containing coating comprises from about 5 mg to about 35 mg of pyridoxine or a salt thereof. In another embodiment, the second active ingredient-containing coating comprises from about 5 mg to about 30 mg of pyridoxine or a salt thereof. In another embodiment, the second active ingredient-containing coating comprises from about 5 mg to about 25 mg of pyridoxine or a salt thereof. In another embodiment, the second active ingredient-containing coating comprises from about 5 mg to about 20 mg of pyridoxine or a salt thereof. In another embodiment, the second active ingredient-containing coating comprises from about 5 mg to about 15 mg of pyridoxine or a salt thereof. In another embodiment, the second active ingredient-containing coating comprises from about 5, 6, 7, 8, 9, 10, 11, 12, 13, 14 or 15 mg of pyridoxine or a salt thereof.

In an embodiment, the second active ingredient-containing coating comprises about 8 to 12 mg (e.g., about 10 mg) of doxylamine or salt thereof such as doxylamine succinate, and about 12 mg to about 16 mg (e.g., about 14-15 mg) of coating material (e.g., OPADRY® film coating).

In an embodiment, the second active ingredient-containing coating is present in an amount of about 2% to about 20% (w/w) of said solid oral dosage form. In further embodiments, the second active ingredient-containing coating is present in an amount of about 5% to about 15%, or about 8% to about 12%, for example about 8, 9, 10, 11 or 12% (w/w), of said solid oral dosage form.

In embodiments, the solid oral dosage form comprises one or more additional coatings/layers.

In an embodiment, the solid oral dosage form further comprises a first intermediate coating surrounding the first active ingredient-containing coating (i.e. between the first- and second-active ingredient-containing coatings). The intermediate coating helps forming a "seal" between the first and second active ingredient-containing coatings so as to avoid or minimize contacts/interactions between the doxylamine component (e.g., doxylamine or salt thereof) and the pyridoxine component (e.g., pyridoxine or salt thereof) comprised in the first and second active ingredient-containing coatings. The intermediate coating may comprise any non-enteric coating material suitable to form a layer or film between the first and second active ingredient-containing coatings, as described above. In an embodiment, the intermediate coating comprises a film coating system comprising a polymer and a plasticizer, for example an OPADRY® film coating system. In an embodiment, the intermediate coating comprises about 5 to 6 mg of the coating material (OPADRY® film coating). In an embodiment, the intermediate coating is present in an amount of about 1% to about 10% (w/w) of said solid oral dosage form. In further embodiments, the intermediate coating is present in an amount of about 1% to about 8%, about 1% to about 5%, or about 2% to about 3 or 4%, for example about 2 or 3% (w/w), of said solid oral dosage form.

In an embodiment, the solid oral dosage form further comprises a seal coating surrounding said second active ingredient-containing coating. The seal coating may comprise any non-enteric coating material suitable to form a layer or film, as described above. In an embodiment, the seal coating comprises a film coating system comprising a polymer and a plasticizer, for example an OPADRY® film coating system. In an embodiment, the seal coating further comprises a dye or pigment (colorant). In an embodiment, the seal coating comprises about 11 to about 15 mg (e.g., about 13 mg) of coating material (e.g., OPADRY® film coating). In an embodiment, the seal coating is present in said solid oral dosage form in an amount of about 1% to about 15% (w/w) of said solid oral dosage form. In further embodiments, the intermediate coating is present in an amount of about 2% to about 10%, about 4% to about 8%, for example about 4, 5, 6, 7 or 8% (w/w), of said solid oral dosage form.

In an embodiment, the solid oral dosage form further comprises a solid oral dosage form- or tablet-coating (e.g., an outer coating) surrounding the seal coating. Such coating may be used, for example, to facilitate the swallowing of the tablet. In an embodiment, the solid oral dosage form- or tablet-coating comprises a wax, for example Carnauba wax. In an embodiment, the solid oral dosage form- or tablet-coating comprises about 0.01 to about 0.05 mg (e.g., about 0.04 mg) of wax material (e.g., Carnauba wax).

In an embodiment, the solid oral dosage form further comprises a second intermediate coating between the core and the enteric coating. The second intermediate coating may comprise any coating material suitable to form a layer or film, as described above. In an embodiment, the second intermediate coating comprises a film coating system comprising a polymer and a plasticizer, for example an OPADRY® film coating system. In an embodiment, the second intermediate coating comprises about 8 mg to about 12 mg (e.g., about 9-10 mg) of coating material (e.g., OPADRY® film coating). In an embodiment, the second intermediate coating is present in an amount of about 1% to about 10% (w/w) of said solid oral dosage form. In further embodiments, the second intermediate coating is present in an amount of about 1% to about 8%, about 1% to about 6%, about 2% to about 6%, for example about 2, 3, 4, 5 or 6% (w/w), of said solid oral dosage form. In an embodiment, the second intermediate coating is present in an amount of about 2% (w/w) of said solid oral dosage form.

The solid oral dosage form may further comprise one or more additional coatings (in addition to those defined herein) or ingredients (excipients).

The term "doxylamine component" (or "doxylamine compound") as used herein refers to doxylamine, doxylamine analogs, derivatives, prodrugs, metabolites and/or salts. The term "pyridoxine component" (or "pyridoxine compound") as used herein refers to pyridoxine, pyridoxine analogs, derivatives, prodrugs, metabolites and/or salts.

The term "analog" or "derivative" as used herein refers to a different compound having a structure similar to that of the "parent" compound (e.g., doxylamine or pyridoxine) but differing from the parent compound in structure (e.g., replacement of one or more atoms by an atom of a different element, presence or absence of a particular group, etc.). An analog/derivative typically exhibits an overall biological effect that is similar to that of the "parent" compound but may differ in one or more physicochemical and/or pharmacokinetic properties (potency, stability, solubility, absorption, in vivo half-life, in vivo distribution, etc.).

"Prodrug" as used herein refers to a compound for administration (which is e.g., in an inactive, or significantly less active form) in a form that, following administration, undergoes chemical conversion by metabolic processes to be transformed into a compound to effect the desired pharmacological activity (e.g., to become an active, or more active, pharmacological agent).

"Metabolite" as used herein refers to a compound resulting from a biochemical conversion of a first compound by metabolic processes/pathways in vivo. A metabolite may differ in one or more physicochemical and/or pharmacokinetic properties (potency, stability, solubility, absorption, in vivo half-life, in vivo distribution, etc.) as compared to the first compound (which may be a prodrug or an active agent). If its structure is known, such a metabolite can be prepared in vitro and administered directly to a subject to exert a biological effect. A given metabolite may itself be metabolized through metabolic processes/pathways, thus resulting in one or more further metabolites that may differ in more or more physico-chemical and/or pharmacokinetic properties as compared to the "first" metabolite.

In an embodiment, the pyridoxine component is a compound of formula I,

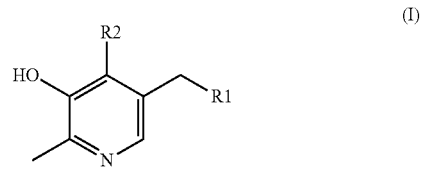

wherein R1 is a hydroxyl (OH) or phosphate ($PO_4^{2-}$ or $HPO_4^-$ or $H_2PO_4$) group; R2 is $CH_2OH$, CHO, or $CH_2NH_2$; and or a pharmaceutically acceptable ester of said compound of formula I, or a pharmaceutically acceptable salt thereof.

As used herein the term "pharmaceutically acceptable salt" refers to a salt of a compound (an active ingredient) that retains the biological activity of the parent compound, and which is not biologically or otherwise undesirable, i.e., is a type of salt and/or is for use in an amount which is not toxic to the subject. In the case of a pregnant human female subject, the pharmaceutically acceptable salt is in concentrations that is not toxic to the embryo or fetus, (i.e., a pharmaceutical salt which is acceptable for administration to a pregnant female) and not contraindicated for use in human pregnancy. Thus, in dosage forms for administration to pregnant subjects, pharmaceutically acceptable salts that have teratogenic properties are excluded.

Pharmaceutically acceptable acid addition salts may be prepared from inorganic and organic acids. Representative acid addition salts include, but are not limited to acetate, adipate, alginate, citrate, aspartate, benzoate, benzenesulfonate, bisulfate, butyrate, camphorate, camphor sulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methane sulfonate, nicotinate, 2-naphthalene sulfonate, oxalate, palm itoate, pectinate, persulfate, 3-phenylpropionate, picrate, pivalate, propionate, succinate, tartrate, thiocyanate, phosphate, glutamate, bicarbonate, p-toluenesulfonate, and undecanoate. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Examples of acids which can be employed to form pharmaceutically acceptable acid addition salts include, for example, an inorganic acid, e.g., hydrochloric acid, hydrobromic acid, sulphuric acid, and phosphoric acid, and an organic acid, e.g., oxalic acid, maleic acid, succinic acid, and citric acid. In an embodiment, the pharmaceutically acceptable salt of doxylamine is doxylamine succinate. In an embodiment, the pharmaceutically acceptable salt of pyridoxine is pyridoxine hydrochloride (pyridoxine HCl).

In an embodiment, the core and the first or second active ingredient-containing coatings comprise the same doxylamine, analog thereof, derivative thereof, prodrug thereof, metabolite thereof or salt thereof (or the same combination of doxylamine, analog thereof, derivative thereof, prodrug thereof, metabolite thereof and/or salt thereof). In another embodiment, the core and the first or second active ingredient-containing coatings comprise different doxylamine, analog thereof, derivative thereof, prodrug thereof, metabolite thereof or salt thereof (or a different combination of doxylamine, analog thereof, derivative thereof, prodrug thereof, metabolite thereof and/or salt thereof). In an embodiment, the core and/or the first or second active ingredient-containing coatings comprise only one of doxylamine, an analog thereof, a derivative thereof, a prodrug thereof, a metabolite thereof or a salt thereof. In an embodiment, the core and/or the first or second active ingredient-containing coatings comprise doxylamine succinate.

In an embodiment, the above-mentioned core and/or first or second active ingredient-containing coatings comprise pyridoxine (PYR) and/or a further medicinal ingredient, such as one or more metabolites of PYR, such as pyridoxine phosphate (PYP), pyridoxal (PYL), pyridoxal 5-phosphate (PLP), pyridoxamine (PYM), pyridoxamine 5-phosphate (PMP), and/or one or more pharmaceutically acceptable salts of PYR, PYP, PYL, PLP, PYM and/or PMP. In an embodiment, the core and/or the first or second active ingredient-containing coatinsg comprise pyridoxal (in addition to one or more of (i) doxylamine, (ii) an analog thereof, (iii) a derivative thereof, (iv) a prodrug thereof, (v) a metabolite thereof and (vi) a salt of any of (i)-(v)). Pyridoxine analogs, derivatives, prodrugs, metabolites and salts include, for example, pharmaceutically acceptable esters or amines of pyridoxine, pyridoxine hydrochloride, pyridoxine phosphate, pyridoxal, pyridoxal phosphate, pyridoxal calcium phosphate, pyridoxal hydrochloride, pyridoxamine, or pyridoxamine dihydrochloride. In an embodiment, the pharmaceutically acceptable salt of pyridoxine is pyridoxine hydrochloride. In an embodiment, the core and the first or second active ingredient-containing coatings comprise the same pyridoxine, metabolite thereof or salt thereof (or the same combination of pyridoxine, metabolite thereof and/or salt thereof), and in a further embodiment the core and the first or second active ingredient-containing coatings comprises pyridoxine or a salt thereof, preferably pyridoxine hydrochloride. In another embodiment, the core and the first or second active ingredient-containing coatings comprise a different pyridoxine, prodrug, metabolite thereof or salt thereof (or a different combination of pyridoxine, prodrug thereof and/or metabolite thereof and/or salt thereof).

In an embodiment, the core comprises pyridoxine hydrochloride and doxylamine succinate, the second active ingredient-containing coating comprises doxylamine succinate and the first active ingredient-containing coating comprises pyridoxine hydrochloride.

The solid oral dosage form comprises a delayed released component, comprising the core and the enteric coating (and optionally the second intermediate coating), and an immediate release component, comprising the first and second active ingredient-containing coatings and the first intermediate coating (and optionally the seal coating, and the solid oral dosage form-coating agent).

The term "immediate release component" or "immediate release composition" as used herein refers to a component/composition of a dosage form that is formulated to release substantially all the active ingredients in a relatively short period on administration with no enhanced, delayed or extended release effect. In some embodiments, the relatively short period can be, for example, within about 0.1 to about 2 hours, e.g., about 10, 15, 20, 30, 40, 60, 90 or 120 minutes. In some embodiments, the immediate release component releases a majority of the active ingredient(s), e.g., at least about 50%, 60%, 70%, 80%, 90%, 95% or 99% of active ingredient(s) from within the dosage form within such a relatively short period after administration. For example, about 80% of the drug can be released within about 30 or 40 minutes after administration, as measured by standard dissolution assays such as those described herein. In an embodiment, the immediate release composition is for effecting release substantially (at least about 90, 91, 92, 93, 94, 95, 96, 97, 98 or 99% is released) within the stomach.

The term "delayed release component" or "delayed release composition" as used herein refers to a component/composition of a dosage form that is formulated so as to have zero or relatively low release of the active ingredients during a period after administration to the subject. The period is typically in the range of about 0.5 to 12 hours, for example in the range of about 1 or 2 hours to about 6, 7, 8 or 9 hours, such as about 1, 2, 3, 4, 5, 6, 7, 8, or 9 hours. In embodiments, the delayed release begins after a period that is from about 2 hours to about 3 hours, or from about 3 hours to about 4 hours, or from about 4 hours to about 5 hours, or from about 5 hours to about 6 hours, after administration. In an embodiment, the delayed release composition is for effecting release substantially within the intestine, i.e., so that there is no or substantially no (less than about 10, 9, 8, 7, 6, 5, 4, 3, 2, or 1%) release in the stomach.

In an embodiment, although the delayed release component from the dosage form commences to dissolve at a later time point than the immediate release component, once release begins, the release pattern of the delayed release component is similar to the pattern of the immediate release component, described above. For example, a relatively short burst duration, for example less than 60 minutes, for instance less than about 50, 40, 30, 20, 15, 10, or 5 minutes, may be characteristic of both immediate release and delayed-burst release.

The immediate release and delayed release compositions result in two sequential releases of the active ingredients, the first release occurring relatively soon after administration and the second release coming later. The time period between the first immediate release of the active ingredients and the subsequent delayed release of the active ingredients can be referred to as the "release interval". In dosage forms of the invention, the release interval can generally be in the range of about 0.5 to 12 hours, for example in the range of about 1 or 2 hours to about 6, 7, 8 or 9 hours, such as about 1, 2, 3, 4, 5, 6, 7, 8, or 9 hours. In embodiments, the delayed release begins after a period that is from about 2 hours to about 3 hours, or from about 3 hours to about 4 hours, or from about 4 hours to about 5 hours, or from about 5 hours to about 6 hours. Optionally, the delayed release is timed to occur at a time when the dosage form is found in the small intestine in fasting and/or fed subjects. The immediate release of active ingredients can for example occur within about 1 hour after administration, for example within about 30 minutes or within about 15 minutes. In an embodiment, the release rate of the doxylamine component is substantially similar (i.e., the difference is less than 10, 9, 8, 7, 6, 5, 4, 3, 2, or 1%) to that of the pyridoxine component (in either one of, or both, the immediate and delayed release components). In an embodiment, the release rate of the doxylamine component is different than that of the pyridoxine component (in either one of, or both, the immediate and delayed release compositions).

The release interval can be determined in vitro or in vivo. Although the plasma concentration of a drug can lag behind the actual time of release in the GI tract, the release interval can be approximately determined in vivo as the time interval between the C. (i.e., the maximum plasma concentration) of the active ingredients achieved by the immediate release component and the $C_{max}$ of the active ingredients achieved by the delayed release component. Alternatively, the release interval can be monitored through the increased plasma concentration of the active ingredients caused by delayed release following immediate release, compared to that achieved by only the immediate release of the active ingredients.

Release can also be assessed using commonly used in vitro dissolution assays. Generally an in vitro dissolution assay is carried out by placing the dosage form(s) (e.g., tablet(s)) in a known volume of dissolution medium in a container with a suitable stirring device. An aliquot of the medium is withdrawn at various times and analyzed for dissolved active substance to determine the rate of dissolution. In one approach, the dosage form (e.g., tablet) is placed into a vessel of a United States Pharmacopeia dissolution apparatus II (Paddles) containing 900 ml dissolution medium at 37° C. The paddle speed is 50, 75 or 100 RPM. Independent measurements are made for at least three (3) tablets, e.g., 6 tablets. The dissolution medium can be a neutral dissolution medium such as 50 mM potassium phosphate buffer, pH 7.2 ("neutral conditions") or water or an acidic medium such as 50 mM potassium (or sodium) acetate buffer, at pH 4.5. Typically a unit dose form is added to the vessel and dissolution is started. At specified times, e.g., 5, 10, 15, 20, 30, 45 or 60 minutes, an aliquot (e.g., 2 ml) of medium is withdrawn and the amount of active ingredient in solution is determined using routine analytical methods (e.g., HPLC).

By way of example, immediate release and/or delayed release of drugs from the dosage form can be monitored using Apparatus II (Paddles) as described in U.S. Pharmacopeia, where the dissolution is conducted by placing one dosage form into each of six vessels containing 900 ml of release media with temperature at 37° C. and speed of 100 rpm. Optionally, the release media of 0.1 N Hydrochloric acid (pH 1.2 or 4.5) is used for stage 1 for 2 hours, and 0.2M tribasic sodium phosphate buffer adjusted to pH6.8 is used for stage 2 (Buffer stage) at 5, 10,15, 20, 30, 45, 60, 90 and 120 minutes and assayed for drug content by HPLC. Further, various media for in vitro dissolution assays (e.g., simulated gastric fluid (SGF), simulated intestinal fluid (SIF), versions to simulate fed or fasting conditions (FeSSGF or FeSSIF for fed conditions, FaSSGF or FaSSIF for fasting conditions), etc.) are well known in the art.

In an embodiment, the solid oral dosage form is monolithic in nature, e.g., in the form of a tablet. Monolithic unit dosage forms may vary in shape and may be, for example, round, ovoid, oblong, cylindrical (e.g., disk shaped) or any other geometric shape, for example rectilinear. For example, the solid oral dosage form can have a disk or ovoid shape, or a shape like a flattened disk or torpedo. The edges can be beveled or rounded.

The active ingredients may conveniently be presented in unit dosage form and may be prepared by any of the methods well known in the art of pharmacy. Techniques and formulations generally are found in for example Remington's Pharmaceutical Sciences (Mack Publishing Co., Easton, Pa.). Such methods include the step of bringing into association of one or more active ingredients with any additional excipients. In general, the dosage forms are prepared by uniformly and intimately bringing into association the active ingredients with liquid carriers or finely divided solid carriers or both, and then shaping the product. In an embodiment, the solid oral dosage form is in tablet form. Various methods of preparation of tablets are well known to one of ordinary skill in the art. See, e.g., Pharmaceutical Dosage Forms: Tablets, Third Edition, by Larry L. Augsburger and Stephen W. Hoag (publisher: Informa Healthcare; Dec. 15, 2007). These methods include direct compression and granulation (e.g., wet or dry or fluid-bed).

The pellets can be made by, for example, simple granulation such as wet granulation or dry granulation, followed by sieving; extrusion and marumerization (spheronization); rotogranulation; or any agglomeration process that results in a pellet of reasonable size and robustness. For extrusion and marumerization, the drug and other additives are granulated by addition of a binder solution. The wet mass is passed through an extruder equipped with a certain size screen, and the extrudates are spheronized in a marumerizer. The resulting pellets are dried and sieved for further applications. One may also use high-shear granulation, wherein the drug and other additives are dry-mixed and then the mixture is wetted by addition of a binder solution in a high shear-granulator/mixer. The granules are kneaded after wetting by the combined actions of mixing and milling. The resulting granules or pellets are dried and sieved for further applications. Alternatively, the immediate release beadlets or pellets are prepared by solution or suspension layering, whereby a solution or dispersion of the active ingredients, with or without a binder and optionally an anti-tacking agent such as talc, is sprayed onto a core or starting seed (either prepared or a commercially available product) in a fluid bed processor or other suitable equipment. The cores or starting seeds can be, for example, sugar spheres or spheres made from microcrystalline cellulose. The active ingredients, thus, are coated on the surface of the starting seeds. The active ingredients may also be layered onto the active ingredients-containing pellets described above, if desired. Following drug layering, the resulting active ingredients-loaded pellets are dried for further applications. A protective layer, or overcoating, may be desired to ensure that the active ingredients-loaded pellets do not aggregate during processing or upon storage. The protective coating layer may be applied immediately outside the core, either an active ingredients-containing core or an active ingredients-layered core, by conventional coating techniques such as pan coating or fluid bed coating using solutions of polymers in water or suitable organic solvents or by using aqueous polymer dispersions. Coating systems such as OPADRY®, OPADRY II® (COLORCON®) and corresponding color and colorless grades from COLORCON® can be used to protect the pellets from being tacky and provide colors to the product. Different anhydride-based polymers (e.g., sebacic/fumaric copolymers such as SPHEROMER™ I or SPHEROMER™ II from SPHERICS, Inc.) may also be used as protective layer. The core (coated or uncoated with a protective coating layer) is then successively coated with the layers/coatings defined herein, e.g., according to the method described in the Examples below.

Dosages may be adjusted to provide the optimum prophylactic/therapeutic response, via administration of a prophylactically or therapeutically effective amount of the active agent(s). A prophylactically or therapeutically effective amount is one in which any toxic or detrimental effects of the active agents (doxylamine and/or pyridoxine component(s)) are outweighed by the prophylactic or therapeutic beneficial effects. For administration to a pregnant human female subject, the effective amount of the active agents is such that it is not toxic to the embryo or fetus.

In an embodiment, the solid oral dosage form comprises about 40 mg or less (e.g., about 35, 30, 25, 20, 15 mg or less) of the doxylamine component, in embodiments between about 10, 11, 12, 13, 14, 15 to about 16, 17, 18, 19, 20, 21, 22, 23, 24, 25, 26, 27, 28, 29 or 30 mg. In an embodiment, the oral dosage form comprises about 20 mg of the doxylamine component (e.g., doxylamine succinate).

In an embodiment, the amount of the doxylamine component, e.g., doxylamine or salt thereof, in the core is from about 5 to about 40 mg, in further embodiments from about 5 to about 30 mg, from about 5 to about 25 mg, from about 5 to about 20 mg, or from about 5 to about 15 mg, for example about 5, 6, 7, 8, 9, 10, 11, 12, 13, 14 or 15 mg. The amount of the doxylamine component, e.g., doxylamine or salt thereof, in the first or second active ingredient-containing coating is from about 5 to about 40 mg, in further embodiments from about 5 to about 30 mg, from about 5 to about 25 mg, from about 5 to about 20 mg, or from about 5 to about 15 mg, for example about 5, 6, 7, 8, 9, 10, 11, 12, 13, 14 or 15 mg, preferably about 10 mg.

In an embodiment, the solid oral dosage form comprises about 40 mg or less (e.g., about 35, 30, 25, 20, 15 mg or less) of the pyridoxine component, in embodiments between about 10, 11, 12, 13, 14, 15 to about 16, 17, 18, 19, 20, 21, 22, 23, 24, 25, 26, 27, 28, 29 or 30 mg. In an embodiment, the oral dosage form comprises about 20 mg of the pyridoxine component (e.g., pyridoxine hydrochloride).

The amount of the pyridoxine component, e.g., pyridoxine or salt thereof, in the core is from about 5 to about 40 mg, in further embodiments from about 5 to about 30 mg, from about 5 to about 25 mg, from about 5 to about 20 mg, or from about 5 to about 15 mg, for example about 5, 6, 7, 8, 9, 10, 11, 12, 13, 14 or 15 mg, preferably about 10 mg.

The amount of the pyridoxine component, e.g., pyridoxine or salt thereof, in the first or second active ingredient-containing coating is from about 5 to about 40 mg, in further embodiments from about 5 to about 30 mg, from about 5 to about 25 mg, from about 5 to about 20 mg, or from about 5 to about 15 mg, for example about 5, 6, 7, 8, 9, 10, 11, 12, 13, 14 or 15 mg, preferably about 10 mg.

In an embodiment, the total weight of the solid oral dosage form is from about 200 mg to about 300 mg, in further embodiment from about 200 mg to about 250 mg or about 220 mg to about 240 mg, for example about 230 mg to about 235 mg.

In an embodiment, the solid oral dosage form comprises:
a core comprising: about 80 to about 100 mg (e.g., about 90 mg) of microcrystalline cellulose; about 5 to about 15 mg (e.g., about 10 mg) of doxylamine or a salt thereof (e.g., doxylamine succinate); about 5 to about 15 mg (e.g., about 10 mg) of pyridoxine or a salt thereof (e.g., pyridoxine hydrochloride); about 0.5 to about 2 mg (e.g., about 1 mg) of colloidal silicon dioxide; about 20 mg to about 30 mg (e.g., about 26-27 mg) of magnesium trisilicate; about 3 mg to about 4 mg (e.g., about 3.5 or 3.6 mg) of croscarmellose sodium; and about 3.5 mg to about 4.5 mg (e.g., about 4 mg) of magnesium stearate;

an enteric coating comprising about 0.001 to about 0.005 mg of antifoaming agent (e.g., simethicone emulsion), about 1 to about 2 mg of plasticizer (e.g., TEC) and about 14 mg to about 15 mg of enteric material/polymer (e.g., Acryl-EZE® enteric coating system);

a first active ingredient-containing coating comprising about 8 to 12 mg (e.g., about 10 mg) of pyridoxine or salt thereof such as pyridoxine HCl, and about 8 mg to about 10 mg (e.g., about 9 mg) of coating material (e.g., OPADRY® film coating);

a first intermediate coating comprises about 5 to 6 mg of a coating material (OPADRY® film coating);

a second active ingredient-containing coating comprising about 8 to 12 mg (e.g., about 10 mg) of doxylamine or salt thereof such as doxylamine succinate, and about 12 mg to about 16 mg (e.g., about 14-15 mg) of coating material (e.g., OPADRY® film coating);

a second intermediate coating (between the core and the enteric coating) comprising about 8 mg to about 12 mg (e.g., about 9-10 mg) of coating material (e.g., OPADRY® film coating);

a seal coating (surrounding the second active ingredient-containing coating) comprising about 11 to about 15 mg (e.g., about 13 mg) of coating material (e.g., OPADRY® film coating); and a solid oral dosage form- or tablet-coating comprises about 0.01 to about 0.05 mg (e.g., about 0.04 mg) of wax material (e.g., Carnauba wax).

In an embodiment, the stability of the solid oral dosage form is preferably such that:
the total amount of related substances (degradation products) of the pyridoxine or salt thereof (e.g., pyridoxine hydrochloride) in the solid oral dosage form kept at 40° C. and 75% relative humidity is about 2% or less after 1, 2, 3 or 6 months;

the total amount of related substances (degradation products) of the doxylamine or salt thereof (e.g., doxylamine succinate) in the solid oral dosage form kept at 40° C. and 75% relative humidity is about 2% or less after 1, 2, 3 or 6 months;

the total amount of related substances (degradation products) of the pyridoxine or salt thereof (e.g., pyridoxine hydrochloride) in the solid oral dosage form kept at 25° C. and 60% relative humidity is about 2% or less after 1, 2, 3 or 6 months;

the total amount of related substances (degradation products) of the doxylamine or salt thereof (e.g., doxylamine succinate) in the solid oral dosage form kept at 25° C. and 60% relative humidity is about 2% or less after 1, 2, 3 or 6 months;

the amount of each unknown related substances (degradation products) in the solid oral dosage form kept at 40° C. and 75% relative humidity is about 0.2% or less after 1, 2, 3 or 6 months; and/or the amount of each unknown related substances (degradation products) in the solid oral dosage form kept at 25° C. and 60% relative humidity is about 0.2% or less after 1, 2, 3 or 6 months.

In another aspect, the present invention provides a method for alleviating the symptoms of nausea and vomiting in a mammal, said method comprising administering an effective amount of the above-mentioned solid oral dosage form to a mammal in need thereof.

In another aspect, the present invention provides a method for alleviating the symptoms of nausea and vomiting of human pregnancy (NVP), the method comprising administering an effective amount of the above-mentioned solid oral dosage form to a pregnant human female in need thereof.

In another aspect, the present invention provides a use of the above-mentioned solid oral dosage form for alleviating the symptoms of nausea and vomiting in a mammal.

In another aspect, the present invention provides a use of the above-mentioned solid oral dosage form for alleviating the symptoms of NVP.

In another aspect, the present invention provides a use of the above-mentioned solid oral dosage form for the preparation of a medicament for alleviating the symptoms of nausea and vomiting in a mammal.

In another aspect, the present invention provides a use of the above-mentioned solid oral dosage form for the preparation of a medicament for alleviating the symptoms of NVP.

In another aspect, the present invention provides the above-mentioned solid oral dosage form for use in alleviating the symptoms of nausea and vomiting in a mammal.

In another aspect, the present invention provides the above-mentioned solid oral dosage form for use in the preparation of a medicament for alleviating the symptoms of NVP.

In another aspect, the present invention provides the above-mentioned solid oral dosage form for use in the preparation of a medicament for alleviating the symptoms of nausea and vomiting in a mammal.

In another aspect, the present invention provides the above-mentioned solid oral dosage form for use in alleviating the symptoms of NVP.

In another aspect, the present invention provides the above-mentioned solid oral dosage form for use as a medicament In another aspect, the present invention provides a package or kit for alleviating the symptoms of nausea and vomiting in a mammal, the package comprising the above-mentioned solid oral dosage form. In an embodiment, the package further comprises instructions for using the solid oral dosage form for alleviating the symptoms of nausea and vomiting in a mammal. The package may further comprise one or more containers.

In another aspect, the present invention provides a package for alleviating the symptoms of nausea and vomiting of human pregnancy (NVP), the kit comprising the above-mentioned solid oral dosage form. In an embodiment, the package further comprises instructions for using the solid oral dosage form for alleviating the symptoms of NVP. The package may further comprise one or more containers.

In an embodiment, the package comprises solid oral dosage forms identified to be taken at different times of the day. For example, the package may comprise a first solid oral dosage form comprising an indicator (shape, color, markings, etc.) that it has to be taken at a certain time of the day (e.g., in the evening, e.g., at about 10 PM), and a second solid oral dosage form comprising an indication (shape, color, markings, etc.) that it has to be taken at another time of the day (e.g., in the morning, e.g., at about 10 AM).

In another embodiment, the package comprises instructions for using the solid oral dosage form according to the following schedule: a first solid oral dosage form in the evening (e.g., at about 10 PM) and a second solid oral dosage form in the morning (e.g., at about 10 AM). The first and second solid oral dosage forms may be the same or different. In an embodiment, the first and second solid oral dosage forms are identical.

In an embodiment, the package further comprises a container in which the above-mentioned solid oral dosage forms are packaged.

In an embodiment, the package comprises a solid oral dosage form bearing pregnancy-friendly indicia to graphically confirm the non-teratogenic aspect of said dosage form. Examples of such pregnancy-friendly indicia are described in PCT publication No. WO/2004/004694. In an embodiment, the indicium is the shape of a graphical illustration of a pregnant woman applied to the dosage form itself or to the container/package.

As used herein, the terms "subject" or "patient" are taken to mean warm blooded animals such as mammals, for example, cats, dogs, mice, guinea pigs, horses, bovine cows, sheep and humans. In an embodiment, the subject is a mammal, and more particularly a female. In a further embodiment, the above-mentioned subject is a human. In yet a further embodiment, the subject is a human female, and more particularly a pregnant human female.

The present invention is illustrated in further details by the following non-limiting examples.

EXAMPLE 1

Stability of Enteric Coated Tablets of Doxylamine Succinate and Pyridoxine HCl

Drug Product Formulation.

Table 1 presents core composition of delayed enteric coated tablets lot ING-028.

TABLE 1

Lot ING-028 enteric-coated Core Tablet Composition

| Ingredient Name | mg/tab |
| --- | --- |
| Core | |
| Doxylamine succinate USP | 10.00 |
| Pyridoxine HCl | 10.00 |
| Microcrystalline cellulose 102 | 90.0 |
| Magnesium trisilicate USP | 26.4 |
| Croscarmellose Sodium | 3.6 |
| Colloidal Silicon Dioxide | 1.0 |
| Magnesium Stearate (Non-Bovine) | 4.0 |
| Total core | 145 |
| Clear coat | |
| Purified water USP | |
| Opadry clear YS-1-7472 | 4.35 |
| Enteric coat | |
| Purified water USP | |
| Simethicone Emulsion 30% USP, | 0.01 |
| Triethyl Citrate NF | 1.66 |
| Acryl-EZE ™ Clear | 14.26 |

Seal Coating.

The enteric-coated core tablets lot ING-028 of Table 1 were coated for an average weight gain of 2.67%, and were renamed L148-02010 SC 20 mg using materials in Table 2.

TABLE 2

Seal Coat Composition Formulation for L148-02010 SC 20 mg

| Ingredient name | Lot | (% w/w) | % solid content |
| --- | --- | --- | --- |
| USP Water | N/A | 93.400 | 0.00%* |
| PlasAcryl T20 ™ (20%) | C00174 | 0.600 | 0.12% |
| Hypromellose (VIVAPHARM ® HPMC E5) | 10056/10 | 6.000 | 6.0% |
| Total | | 100.000 | 6.12% |

*removed during coating and drying processes

Immediate Release Layer Coating.

A target immediate release (IR) composed of 10 mg of Doxylamine succinate and 10 mg of Pyridoxine HCl was applied on the seal coated tablet lot L148-02010 SC 20 mg, which were renamed lot L148-02010A bimodal FCT IR & DR 40 mg. The actual average amount of both active pharmaceutical ingredients (APIs) (doxylamine succinate and pyridoxine HCl) applied per one tablet was 26.2 mg, included overage. The composition of the IR layer coat is presented in Table 3.

TABLE 3

IR Layer Coat Composition Formulation for
L148-02010A Bimodal FCT IR & DR 40 mg

| Ingredient | Lot | (% w/w) | % solid content |
|---|---|---|---|
| USP Water | N/A | 78.1 | 0.00%* |
| Doxylamine succinate | 1045 | 5.0 | 5.00% |
| Pyridoxine HCl | 11MP039 | 5.0 | 5.00% |
| Hypromellose (Vivapharm HPMC E5) | 10056/10 | 6.0 | 6.00% |
| PlasAcryl T20 ™ (20%), | C00174 | 5.9 | 1.18% |
| Total | | 100.0 | 17.18% |

*removed during coating and drying processes

Finishing Coating.

The Diclectin FCT bimodal IR & DR 40 mg lot L148-02010A was then over layer coated with an average weight of 1.4% weight gain from a 5% (w/w) of aqueous suspension of OPADRY® YS-1-18027-A white lot TS060604. Finally, a finishing layer of 0.1% of Carnauba Wax powder lot 14613 was applied on the tablets.

Stability Program.

An R&D stability study was initiated for the coated Diclectin bimodal tablets IR & DR 40 mg lot L148-02010A for up to a 12-month period under long term (25° C/60% relative humidity (RH)), and a 6 month period under accelerated (40° C./75%RH) conditions to evaluate stability results of new drug products.

The tablets were packaged in 60 cc round white opaque high density polyethylene (HDPE) bottles (Lot C00139, Drug Plastic & Glass Co.) and induction sealed with polypropylene caps child resistant (Lot C00137, Drug Plastic & Glass Co.). The bottles were then placed in controlled environment chambers.

The following methods were used:

Visual observation for Appearance;

Assay and Related Substances. Assay and Degradation products (Related Substances) for doxylamine succinate and Pyridoxine HCl was determined using High Performance Liquid Chromatography (HPLC) equipped with UV detector. The HPLC column used was an Inertsi™ ODS2, (150× 4.6 mm, 5 um), flow 1.0 mL/min. It was performed under gradient at 291 nm for 0-10 min. and 261 nm for 10-45 min. The typical retention is approx. 6 minutes for Pyridoxine HCl and 28 minutes for Doxylamine succinate; and Dissolution. Acid stage: 100 rpm paddle, 900 mL 0.1 N HCl; and Buffer stage: 100 rpm paddle, 900 mL Phosphate buffer pH 6.8: Non USP buffer preparation: 0.2M $Na_3PO_4$: 0.1N HCl 1:3, pH 6.8).

Tables 4A and 4B present available stability results of samples stored under accelerated (Table 4A) and long term (Table 4B) stability conditions up to 6 months. Content uniformity values at T=0 showed acceptable variability. ND=not detected; NA=not applicable (not tested); RRT=relative retention time; % LC=% Label Claim; RSD=relative standard deviation and AV=acceptable value.

TABLE 4A

Stability Results at T = 0, T = 1,
T = 2 and T = 6 months at 40° C./75% RH

| Sample Formulation Dose strength | | L148-02010A-IR-DR IR (10/10)-DR (10/10) FCT Pyridoxine HCl 20 mg Doxylamine succinate 20 mg | | | |
|---|---|---|---|---|---|
| Active | | Pyridoxine HCl | | Doxylamine succinate | |
| Storage | Time point | | | | |
| Appearance (Organoleptic) | T = 0 | Off-white round tablet with mottled specks | | | |
| | 1 month | Off-white round tablet with mottled specks | | | |
| | 2 months | Off white-brownish round biconvex tablets | | | |
| | 6 months | Not tested | | | |
| Uniformity of Dosage Unit | | % LC (By Content) | | % LC (By Content) | |
| NPLC-988 (% Label Claim) (USP <905> AV: Acceptable value ≤15) | T = 0 | 113.3 | 107.3 | 108.2 | 101.3 |
| | | 110.6 | 109.0 | 106.4 | 103.9 |
| | | 111.4 | 108.9 | 107.2 | 105.7 |
| | | 107.5 | 110.0 | 102.8 | 104.0 |
| | | 111.5 | 109.6 | 105.8 | 105.8 |
| | | minimum | 107.3 | minimum | 101.3 |
| | | maximum | 113.3 | maximum | 108.2 |
| | | mean | 109.9 | mean | 105.1 |
| | | RSD | 1.7 | RSD | 2.0 |
| | | AV | 13 | AV | 9 |
| Assay Diluent pH 6.8/30% Methanol | T = 0 | 108.4% | | 105.0% | |
| | 1 month | 106.9% | | 108.7% | |
| | 2 months | 105.2% | | 107.3% | |
| | 6 months | 100.9% | | 106.1% | |
| Related Substances | T = 0 | Total: 0.12% area | | Total: 0.08% area | |
| | | Largest impurity: 0.12% area @ RRT 1.44 | | Largest impurity: 0.08% area @ RRT 1.04 | |
| | | RRT | % area | RRT | % area |
| | | 0.85 | <0.05 | 1.04 | 0.08 |
| | | 1.22 | <0.05 | 1.08 | <0.05 |
| | | 1.30 | <0.05 | | |
| | | 1.36 | ND | | |
| | | 1.44 | 0.12 | | |
| | | Total | 0.12 | Total | 0.08 |
| | 1 month | Total: 1.16% area Largest impurity: 0.75% area @ RRT 1.44 | | Total: 0.45% area Largest impurity: 0.30% area @ RRT 0.56 | |
| | | RRT | % area | RRT | % area |
| | | 0.85 | <0.05 | 0.56 | 0.30 |
| | | 1.22 | 0.25 | 1.08 | 0.15 |
| | | 1.30 | 0.15 | | |
| | | 1.36 | ND | | |
| | | 1.44 | 0.75 | | |
| | | Total | 1.16 | Total | 0.45 |

TABLE 4A-continued

Stability Results at T = 0, T = 1, T = 2 and T = 6 months at 40° C./75% RH

| | | | | |
|---|---|---|---|---|
| 2 months | Total 0.87% area Largest impurity: 0.33% area @ RRT 1.44 | | Total 0.98% area Largest impurity: 0.71% area @ RRT 0.57 | |
| | RRT | % area | RRT | % area |
| | 0.85 | 0.06 | 0.56 | 0.71 |
| | 1.22 | 0.14 | 0.70 | 0.08 |
| | 1.30 | 0.25 | 0.72 | 0.06 |
| | 1.36 | 0.09 | 1.04 | ND |
| | 1.44 | 0.33 | 1.08 | 0.13 |
| | Total | 0.87 | Total | 0.98 |
| 6 months | Total: 0.59% area Largest impurity: 0.20% area @ RRT 1.44 | | Total: 1.88% area Largest impurity: 1.28% area @ RRT 0.56 | |
| | RRT | % area | RRT | % area |
| | 0.85 | ND | 0.56 | 1.28 |
| | 1.22 | 0.07 | 0.70 | ND |
| | 1.30 | 0.19 | 0.72 | ND |
| | 1.36 | 0.13 | 1.04 | ND |
| | 1.44 | 0.20 | 1.08 | 0.59 |
| | Total | 0.59 | Total | 1.88 |

| Dissolution IR Acid Stage | | Time (min.) | % LC | Time (min.) | % LC |
|---|---|---|---|---|---|
| 900 ml 0.1N HCl Paddles at 100 rpm | T = 0 | 120 | 120 | 120 | 117 |
| | 1 month | 120 | 112 | 120 | 113 |
| | 2 months | 120 | 111 | 120 | 117 |
| Dissolution DR Buffer Stage (following exposure to acid stage) 900 ml Phosphate Buffer pH 6.8[1] Paddles at 100 rpm | T = 0 | 45 | 102 | 45 | 102 |
| | 1 month | 45 | 101 | 45 | 99 |
| | 2 months | 45 | 97 | 45 | 99 |

[1] Non USP buffer preparation: 0.2M Na$_3$PO$_4$:0.1N HCl 1:3, pH 6.8

TABLE 4B

Stability Results at T = 0, T = 1, T = 2 and T = 6 months at 25° C./60% RH

| | | | |
|---|---|---|---|
| Sample | | L148-02010A-IR-DR | |
| Formulation | | IR (10/10)-DR(10/10) FCT | |
| Dose strength | | Pyridoxine HCl 20 mg Doxylamine succinate 20 mg | |
| Active | | Pyridoxine HCl | Doxylamine succinate |
| Storage | Time point | | |
| Appearance (Organoleptic) | T = 0 | Off-white round tablet with mottled specks | |
| | 1 month | NA | |
| | 2 months | Off white-greyish round biconvex tablets | |
| | 6 months | Not tested | |
| Uniformity of Dosage Unit | | % LC (By Content) | % LC (By Content) |
| NPLC-988 (% Label Claim) (USP <905> AV: Acceptable value ≤15) | T = 0 | 113.3 110.6 111.4 107.5 111.5 minimum maximum mean RSD AV | 107.3 109.0 108.9 110.0 109.6 107.3 113.3 109.9 1.7 13 | 108.2 106.4 107.2 102.8 105.8 minimum maximum mean RSD AV | 101.3 103.9 105.7 104.0 105.8 101.3 108.2 105.1 2.0 9 |
| Assay Diluent pH 6.8/30% Methanol | T = 0 | 108.4% | 105.0% |
| | 1 month | NA | NA |
| | 2 months | 108.6% | 107.5% |
| | 6 months | 108.1% | 107.1% |
| Related Substances | T = 0 | Total: 0.12% area | Total: 0.08% area |

TABLE 4B-continued

Stability Results at T = 0, T = 1,
T = 2 and T = 6 months at 25° C./60% RH

|  |  | Largest impurity: 0.12% area @ RRT 1.44 | | Largest impurity: 0.08% area @ RRT 1.04 | |
| --- | --- | --- | --- | --- | --- |
|  |  | RRT | % area | RRT | % area |
|  |  | 0.85 | <0.05 | 1.04 | 0.08 |
|  |  | 1.22 | <0.05 | 1.08 | <0.05 |
|  |  | 1.30 | <0.05 |  |  |
|  |  | 1.36 | ND |  |  |
|  |  | 1.44 | 0.12 |  |  |
|  |  | Total | 0.12 | Total | 0.08 |
|  | 1 month | NA | | NA | |
|  | 2 months | Total: 0.36% area Largest impurity: 0.18% area @ RRT 1.44 | | Total: 0.08% area Largest impurity: 0.08% area @ RRT 1.08 | |
|  |  | RRT | % area | RRT | % area |
|  |  | 0.85 | ND | 0.56 | ND |
|  |  | 1.22 | 0.06 | 0.70 | ND |
|  |  | 1.30 | 0.12 | 0.72 | ND |
|  |  | 1.36 | ND | 1.04 | ND |
|  |  | 1.44 | 0.18 | 1.08 | 0.08 |
|  |  | Total | 0.36 | Total | 0.08 |
|  | 6 months | Total: 0.59% area Largest impurity: 0.20% area @ RRT 1.44 | | ND | |
|  |  | RRT | % area | RRT | % area |
|  |  | 0.85 | ND | 0.56 | ND |
|  |  | 1.22 | 0.07 | 0.70 | ND |
|  |  | 1.30 | 0.19 | 0.72 | ND |
|  |  | 1.36 | 0.13 | 1.04 | ND |
|  |  | 1.44 | 0.20 | 1.08 | ND |
|  |  | Total | 0.59 | Total | ND |

| Dissolution IR Acid Stage |  | Time (min.) | % LC | Time (min.) | % LC |
| --- | --- | --- | --- | --- | --- |
| 900 ml 0.1N HCl Paddles at 100 rpm | T = 0 | 120 | 120 | 120 | 117 |
|  | 1 month | NA | | NA | |
|  | 2 months | 120 | 118 | 120 | 118 |
| Dissolution DR Buffer Stage | T = 0 | 45 | 102 | 45 | 102 |
|  | 1 month | NA | | NA | |
| (following exposure to acid stage) 900 ml Phosphate Buffer pH 6.8[1] Paddles at 100 rpm | 2 months | 45 | 99 | 45 | 101 |

[1] Non USP buffer preparation: 0.2M $Na_3PO_4$:0.1N HCl 1:3, pH 6.8

Summary of Results

At T=1 month, no significant changes were observed for appearance, assay and dissolution tests. An increase in related substances was measured for both doxylamine succinate and pyridoxine hydrochloride under accelerated conditions, but was more prominent for Pyridoxine HCl (1.16% vs. 0.45% for Doxylamine succinate).

At T=2 months, under accelerated conditions (40° C./75% RH), the appearance of tablets became off-white brownish but the assay and the dissolution results for both APIs remained unchanged. Between 1 month and 2 months, the total related substances of Doxylamine succinate doubled from 0.45% to 0.98%, and the total related substances of Pyridoxine HCl slightly decreased from 1.16% down to 0.87%.

At T=2 months for samples under long term stability conditions (25° C./60% RH), the total related substances of Pyridoxine HCl increased from 0.12% to 0.36%. A slight change in appearance to off-white greyish tablets was observed.

At T=6 months, there was no noticeable change observed under both stability conditions evaluated for the assay. However, in one hand, while the total related substances of Pyridoxine HCl continued to decrease when compared to T=1 months under accelerated conditions (from 1.16% down to 0.59% area), it appeared that heat and humidity had a significant impact in increasing the related substances of Doxylamine succinate from 0.45% up to 1.88% area with time. On the other hand and in long term stability conditions, while the Pyridoxine HCl presented a moderate raise of related substances (0.59% when compared to 0.12% area at T=0), the Doxylamine succinate proved to be relatively stable up to 6 months with NMT 0.08% area of total related substances.

The results above showed that the degradation product profile of Doxylamine succinate and Pyridoxine HCl did not follow an expected profile compared to substantial volume of historical data from Diclectin®/Diclegis®, indicating that the coating process used for the preparation of this formulation is not acceptable.

EXAMPLE 2

Analytical Testing of Doxylamine Succinate and Pyridoxine HCl Coating Solutions

To investigate the unexpected results of Example 1, considering stability of the 2 APIs (doxylamine succinate and pyridoxine hydrochloride) in the core tablet of Diclectin®/Diclegis®, the hypothesis was that the possible drug-drug interaction in the coating solution. Therefore various coating solutions with different API combination at different pH were prepared and tested. For each test, assay and degradation product analyses were performed under the following stability conditions: 24 hrs and 48 hrs at ambient temperature, 4 days at 40° C. and 2 hours at 50° C.

Test 1 (Coating Suspension A): coating solution used for the formulations of Example 1 (doxylamine succinate 50 mg/g +pyridoxine HCl 50 mg/g).

Test 2 (Coating Suspension B): doxylamine succinate 50 mg/g+pyridoxine HCl 50 mg/g with pH lowered to 2.5.

Test 3 (Coating Suspension C): doxylamine succinate 50 mg/g+pyridoxine HCl 50 mg/g with pH raised to 12.3.

Test 4 (Coating Suspension D): doxylamine succinate 64 mg/g+pyridoxine HCl 64 mg/g in water.

Test 5 (Coating Suspension E): pyridoxine HCl 50 mg/g only in water.

Test 6 (Coating Suspension F): doxylamine succinate 50 mg/g only in water.

All sample solutions were prepared by dissolving 0.5 g of the suspension or solution in 100 ml of diluent (0.1% phosphoric acid in water) and filtered. The results of the tests are depicted in Tables 5A to 5F.

TABLE 5A

Stability results for coating suspension A

| Sample | | L148-02 Coating Suspension Suspension A |
| --- | --- | --- |
| Formulation | | Coating Suspension As per formulation of Example 1 |
| Dose strength | | Pyridoxine HCl 50 mg/g Doxylamine succinate 50 mg/g |
| Appearance | T = 0 | White suspension |
| | T = 24 hrs ambient | Light pink colored suspension |
| | T = 48 hrs ambient | Light pink colored suspension |
| | 4 days at 40° C. | Light tan colored suspension |
| | 2 hours 50° C. | Tan colored suspension |

| | | Pyridoxins HCl | | Doxylamine succinate |
| --- | --- | --- | --- | --- |
| Assay (% Label Claim) | T = 0 | 104.3% (52.2 mg/g) | | 105.3% (52.6 mg/g) |
| | T = 24 hrs | 105.7% (52.8 mg/g) | | 106.9% (53.4 mg/g) |
| | T = 48 hrs | 104.2% (52.1 mg/g) | | 105.0% (52.5 mg/g) |
| | 4 days at 40° C. | 103.5% (51.7 mg/ml) | | 105.0% (52.5 mg/ml) |
| | 2 hours 50° C. | 105.3% (52.7 mg/ml) | | 106.6% (53.3 mg/ml) |
| Related Substances (% Label Claim) | T = 0 | No peaks ≥0.05% | | No peaks ≥0.05% |
| | T = 24 hrs | No peaks ≥0.05% | | No peaks ≥0.05% |
| | T = 48 hrs | No peaks ≥0.05% | | No peaks ≥0.05% |
| | 4 days at 40° C. | RRT 1.22 1.44 | % LC 0.11 0.14 | No peaks ≥0.05% |
| | | Total | 0.25 | |
| | 2 hours 50° C. | RRT 1.22 1.44 | % LC 0.08 0.07 | No peaks ≥0.05% |
| | | Total | 0.15 | |

TABLE 5B

Stability results for coating suspension B

| Sample | | L148-02 Coating Suspension Suspension B |
| --- | --- | --- |
| Formulation | | Coating Suspension pH lowered to 2.5 |
| Dose strength | | Pyridoxins HCl 50 mg/g Doxylamine succinate 50 mg/g |
| Appearance | T = 0 | White suspension |
| | T = 24 hrs ambient | White suspension |
| | T = 48 hrs ambient | White suspension |
| | 4 days at 40° C. | White suspension |
| | 2 hours 50° C. | White suspension |

TABLE 5B-continued

Stability results for coating suspension B

| | | Pyridoxine HCl | Doxylamine succinate |
|---|---|---|---|
| Assay (% Label Claim) | T = 0 | 100.5% (50.3 mg/g) | 101.0% (50.5 mg/g) |
| | T-24 hrs ambient | 102.1% (51.1 mg/g) | 102.6% (51.3 mg/g) |
| | T = 48 hrs ambient | 100.1% (50.1 mg/g) | 100.4% (50.2 mg/g) |
| | 4 days at 40° C. | 101.7% (50.8 mg/ml) | 102.2% (51.1 mg/ml) |
| | 2 hours 50° C. | 101.1% (50.6 mg/ml) | 101.8% (50.9 mg/ml) |
| Related Substances (% Label Claim) | T = 0 | No peaks ≥0.05% | No peaks ≥0.05% |
| | T = 24 hrs ambient | No peaks ≥0.05% | No peaks ≥0.05% |
| | T = 48 hrs ambient | No peaks ≥0.05% | No peaks ≥0.05% |
| | 4 days at 40° C. | RRT 1.22 %LC 0.10; RRT 1.44 %LC 0.08; Total 0.18 | No peaks ≥0.05% |
| | 2 hours 50° C. | RRT 1.22 %LC 0.07; RRT 1.44 %LC 0.03; Total 0.10 | No peaks ≥0.05% |

TABLE 5C

Stability results for coating suspension C

| Sample | L148-02 Coating Suspension Suspension C |
|---|---|
| Formulation | Coating Suspension pH raised to 12.3 |
| Dose strength | Pyridoxins HCl 50 mg/g; Doxylamine succinate 50 mg/g |

| Appearance | | |
|---|---|---|
| | T = 0 | Pale yellow suspension |
| | T = 24 hrs ambient | Pale yellow suspension |
| | T = 48 hrs ambient | Pale yellow suspension |
| | 4 days at 40° C. | Pale yellow suspension |
| | 2 hours 50° C. | Pale yellow suspension |

| | | Pyridoxins HCl | Doxylamine succinate |
|---|---|---|---|
| Assay (% Label Claim) | T = 0 | 93.5% (46.8 mg/g) | 94.0% (47.0 mg/g) |
| | T = 24 hrs ambient | 94.4% (47.2 mg/g) | 95.2% (47.6 mg/g) |
| | T = 48 hrs ambient | 92.6% (46.3 mg/g) | 93.2% (46.6 mg/g) |
| | 4 days at 40° C. | 94.0% (47.0 mg/g) | 95.4% (47.7 mg/g) |
| | 2 hours 50° C. | 94.1% (47.0 mg/ml) | 94.1% (47.1 mg/ml) |
| Related Substances (% Label Claim) | T = 0 | No peaks ≥0.05% | 1 peak 0.06% @ RRT 0.74 |
| | T = 24 hrs ambient | No peaks ≥ 0.05% | 1 peak 0.12% @ RRT 0.74 |
| | T = 48 hrs ambient | No peaks ≥0.05% | 1 peak 0.14% @RRT 0.74 |

TABLE 5C-continued

Stability results for coating suspension C

| | | | |
|---|---|---|---|
| 4 days at 40° C. | No peaks ≥0.05% | 1 peak 0.22% @ RRT 0.72 | |
| 2 hours 50° C. | No peaks ≥0.05% | RRT 0.72 %LC 0.20; RRT 1.04 %LC 0.08; Total 0.28 | |

TABLE 5D

Stability results for coating suspension D

| Sample | L148-02 Solution Solution D |
|---|---|
| Formulation | Solution in Water, pH 4.4 |
| Dose strength | Pyridoxine HCl 64 mg/kg; Doxylamine succinate 64 mg/g |

| Appearance | | |
|---|---|---|
| | T = 0 | Clear solution |
| | T = 24 hrs ambient | Solution with precipitate |
| | T = 48 hrs ambient | Solution with precipitate |
| | 4 days at 40° C. | Pale amber, clear solution |
| | 2 hours 50° C. | Pale amber, clear solution |

| | | Pyridoxine HCl | Doxylamine succinate |
|---|---|---|---|
| Assay (% Label Claim) | T = 0 | 98.5% (63.1 mg/g) | 99.1% (63.5 mg/g) |
| | T = 24 hrs ambient | 107.5% (68.8 mg/g) | 99.9% (63.9 mg/g) |
| | T = 48 hrs ambient | 98.1% (62.8 mg/g) | 99.7% (63.8 mg/g) |
| | 4 days at 40° C. | 86.6%[1] (55.4 mg/ml) | 87.5%[1] (62.4 mg/ml) |
| | 2 hours 50° C. | 103.0% (65.9 mg/ml) | 99.7% (64.1 mg/ml) |
| Related Substances (% Label Claim) | T = 0 | No peaks ≥0.05% | No peaks ≥0.05% |
| | T = 24 hrs ambient | No peaks ≥0.05% | No peaks ≥0.05% |
| | T = 48 hrs ambient | No peaks ≥0.05% | No peaks ≥0.05% |
| | 4 days at 40° C. | RRT 1.22 %LC 0.09; RRT 1.44 %LC 0.11; Total 0.21 | No peaks ≥0.05% |
| | 2 hours 50° C. | RRT 1.22 %LC 0.07; RRT 1.44 %LC 0.06; Total 0.13 | No peaks ≥0.05% |

TABLE 5E

Stability results for coating suspension E

| Sample | L148-02 Solution Solution E |
|---|---|
| Formulation | Solution in Water, pH 2.8 Pyridoxine HCl only |
| Dose strength | Pyridoxine HCl 50 mg/g |

| Appearance | | |
|---|---|---|
| | T = 0 | Clear solution |
| | T = 24 hrs ambient | Clear solution |

TABLE 5E-continued

Stability results for coating suspension E

| | T = 48 hrs ambient | Clear solution |
|---|---|---|
| | 4 days at 40° C. | Clear solution |
| | 2 hours 50° C. | Clear solution |

| | | Pyridoxine HCl | Doxylamine succinate |
|---|---|---|---|
| Assay (% Label Claim) | T = 0 | 98.3% (49.1 mg/g) | N/A |
| | T = 24 hrs ambient | 100.7% (50.3 mg/g) | N/A |
| | T = 48 hrs ambient | 100.1% (50.1 mg/g) | N/A |
| | 4 days at 40° C. | 100.8% (50.4 mg/ml) | N/A |
| | 2 hours 50° C. | 100.6% (50.3 mg/ml) | N/A |
| Related Substances (% Label Claim) | T = 0 | No peaks ≥0.05% | N/A |
| | T = 24 hrs ambient | No peaks ≥0.05% | N/A |
| | T = 48 hrs ambient | No peaks ≥0.05% | N/A |
| | 4 days at 40° C. | No peaks ≥0.05% | N/A |
| | 2 hours 50° C. | No peaks ≥0.05% | N/A |

TABLE 5F

Stability results for coating suspension F

| Sample | | L148-02 Solution Solution F |
|---|---|---|
| Formulation | | Solution in Water, pH 5.0 Doxylamine succinate only |
| Dose strength | | Doxylamine succinate 50 mg/g |
| Appearance | T = 0 | Clear solution |
| | T = 24 hrs ambient | Clear solution |
| | T = 48 hrs ambient | Clear solution |
| | 4 days at 40° C. | Clear solution |
| | 2 hours 50° C. | Clear solution |

| | | Pyridoxine HCl | Doxylamine succinate |
|---|---|---|---|
| Assay (% Label Claim) | T = 0 | N/A | 99.1% (49.6 mg/g) |
| | T = 24 hrs ambient | N/A | 98.5% (49.2 mg/g) |
| | T = 48 hrs ambient | N/A | 100.1% (49.2 mg/g) |
| | 4 days at 40° C. | N/A | 100.7% (50.4 mg/ml) |
| | 2 hours 50° C. | N/A | 101.4% (50.7 mg/ml) |
| Related Substances (% Label Claim) | T = 0 | N/A | No peaks ≥0.05% |
| | T = 24 hrs ambient | N/A | No peaks ≥0.05% |
| | T = 48 hrs ambient | N/A | No peaks ≥0.05% |
| | 4 days at 40° C. | N/A | No peaks ≥0.05% |
| | 2 hours 50° C. | N/A | No peaks ≥0.05% |

The results from these tests indicate that when doxylamine and pyridoxine are together in solution, degradation products are present for pyridoxine and/or doxylamine, showing drug-drug interaction in all solutions.

EXAMPLE 3

Analytical Testing of a Formulation Comprising Doxylamine Succinate and Pyridoxine HCl in Separate Layers/Coatings To overcome the issue noted above, new prototype formulations were prepared, in which the active ingredients (doxylamine succinate and pyridoxine HCl) were added as individual solutions and added as successive coats with a protective coat in between. The prototype formulations were prepared with the successive addition of the following layers coating the enteric-coated core tablet (lot ING-028, Table 1):

Layer 1: seal coat (3%),

Layer 2: pyridoxine HCl 37.5 g/batch solution,

Layer 3: seal coat (3%),

Layer 4: doxylamine succinate 40 g/batch,

Layer 5: Opadry white over layer (6%),

Layer 6: carnauba wax (0.1%).

The first lot of these prototypes (lot 02016A) was put in stability testing under long term (25° C./60% RH) and accelerated (40° C./75% RH) conditions. The results from the stability studies are depicted in Tables 6A to 6D.

TABLE 6A

Stability Results for Pyridoxine HCl at T = 0, T = 1, T = 2, T = 3 and T = 6 months at 40° C./75% RH

| | Levels | | | | |
|---|---|---|---|---|---|
| RRT | 0 month | 1 month | 2 months | 3 months | 6 months |
| 0.28-0.29 | <LOQ | <LOQ | 0.01 | <LOQ | <LOQ |
| 0.30 | 0.1 | 0.02 | | 0.02 | 0.02 |
| 0.31-0.32 | <LOQ | 0.01 | 0.02 | 0.01 | 0.01 |
| 0.323 | | | | | 0.01 |
| 0.34-0.35 | <LOQ | <LOQ | <LOQ | <LOQ | 0.02 |
| 0.73-0.75 | <LOQ | <LOQ | <LOQ | <LOQ | 0.01 |
| 0.80-0.83 | 0.02 | 0.02 | <LOQ | <LOQ | 0.06 |
| 0.84-0.85 | 0.04 | 0.04 | 0.09 | 0.12 | 0.12 |
| 0.87-0.89 | | | 0.01 | | |
| 1.19-1.22 | <LOQ | 0.02 | 0.03 | 0.02 | 0.05 |
| 1.28-1.30 | 0.02 | <LOQ | <LOQ | <LOQ | <LOQ |
| 1.41-1.44 | 0.02 | 0.08 | 0.11 | 0.12 | 0.21 |
| 1.49-1.52 | <LOQ | <LOQ | <LOQ | <LOQ | 0.01 |
| Total | 0.2 | 0.2 | 0.27 | 0.29 | 0.52 |

RTT = relative retention time
LOQ = limit of quantification

TABLE 6B

Stability Results for Pyridoxine HCl at T = 0, T = 3 and T = 6 months at 25° C./60% RH

| RRT | 0 month | 3 months | 6 months |
|---|---|---|---|
| 0.30 | 0.1 | 0.03 | 0.01 |
| 0.31-0.32 | <LOQ | | 0.01 |
| 0.80-0.83 | 0.02 | <LOQ | 0.02 |
| 0.84-0.85 | 0.04 | 0.07 | 0.06 |
| 0.87-0.89 | | 0.01 | |
| 1.15 | | | |
| 1.28-1.30 | 0.02 | <LOQ | <LOQ |
| 1.41-1.44 | 0.02 | 0.04 | 0.05 |
| 1.49-1.52 | <LOQ | <LOQ | <LOQ |
| Total | 0.2 | 0.15 | 0.15 |

TABLE 6C

Stability Results for Doxylamine succinate at T = 0, T = 1, T = 2, T = 3 and T = 6 months at 40° C./75% RH

| RRT | 0 month | 1 month | 2 months | 3 months | 6 months |
|---|---|---|---|---|---|
| 0.57-0.60 | <LOQ | 0.1 | 0.12 | 0.18 | 0.39 |
| 0.70-0.72 | 0.03 | 0.1 | 0.16 | 0.21 | 0.38 |
| 0.71-0.74 | <LOQ | <LOQ | <LOQ | 0.03 | 0.08 |
| 0.78-0.79 | | 0.02 | 0.03 | 0.03 | 0.06 |
| 0.81-0.82 | | <LOQ | <LOQ | | |
| 0.82-0.83 | 0.03 | <LOQ | <LOQ | | 0.03 |
| 0.85-0.86 | <LOQ | <LOQ | <LOQ | <LOQ | 0.04 |
| 0.91 | <LOQ | <LOQ | <LOQ | <LOQ | 0.07 |
| 0.96-0.97 | <LOQ | <LOQ | <LOQ | 0.03 | 0.05 |
| 1.03-1.05 | 0.1 | <LOQ | <LOQ | <LOQ | <LOQ |
| 1.04-1.05 | <LOQ | 0.1 | 0.08 | 0.05 | 0.04 |
| 1.08 | 0.03 | 0.04 | 0.06 | 0.06 | 0.09 |
| Total | 0.2 | 0.4 | 0.45 | 0.59 | 1.21 |

TABLE 6D

Stability Results for Doxylamine succinate at T = 0, T = 3 and T = 6 months at 25° C./60% RH

| RRT | 0 month | 3 months | 6 months |
|---|---|---|---|
| 0.57-0.60 | <LOQ | <LOQ | 0.02 |
| 0.70-0.72 | 0.03 | 0.04 | 0.07 |
| 0.82-0.83 | 0.03 | 0.03 | 0.03 |
| 1.03-1.05 | 0.1 | <LOQ | <LOQ |
| 1.04-1.05 | <LOQ | 0.06 | 0.07 |
| 1.08 | 0.03 | 0.03 | 0.03 |
| Total | 0.2 | 0.16 | 0.22 |

The above results under accelerated and long term conditions clearly show that after 6 months the amounts of related substances in the formulations remain at an acceptable level using the improved coating process.

EXAMPLE 4

Preparation of Tablet Cores

Tablets cores were produced as using the ingredients shown in Table 7.

TABLE 7

| | Ingredients | Weight per batch* (kg) | Weight per tablet (mg) |
|---|---|---|---|
| 1A | Microcrystalline cellulose 102 | 46.5 | 90 |
| 1B | | 46.6 | |
| 2 | Doxylamine Succinate USP | 10.345 | 10.0 |
| 3 | Colloidal Silicon Dioxide | 1.035 | 1.0 |
| 4 | Pyridoxine HCl | 10.345 | 10.0 |
| 5 | Magnesium trisilicate USP | 27.31 | 26.4 |
| 6 | Croscarmellose sodium | 3.724 | 3.6 |
| 7A | Magnesium stearate non-bovine | 2.000 | 4.0 |
| 7B | | 2.136 | |
| | Total weight | 150.00 | 145.0 |

*Batch size: 1 034 462 tablets

First, ingredient 1A was processed using a Quadro™ Comil U10 with 024R screen and collected.

Then, ingredients 2, 3 and 4 were mixed together. This mixture was then processed using the Comil™ U10 and added to ingredient 1A.

Ingredient 1B was processed using the Comil™ U10 and added to the mixture obtained step 2. The new mixture thus produced was then mixed.

Ingredients 5 and 6 were mixed together and then added to the mixture obtained in step 3. The new mixture thus produced was then mixed.

Ingredient 7A was added to the mixture obtained in step 4. The new mixture thus produced was then mixed.

The mixture obtained in step 5 was then compacted with a Gerteis™ Mini-Pactor with grooved rollers and 1000 micron mesh screen.

The compacted material was then collected and mixed with ingredient 7B.

Compressed tablets were then produced using a Manesty™ Diamon Unipress press equipped with 5/16" round standard concave, plain upper and lower punches. The target hardness was 7 kp.

EXAMPLE 5

Tablet Coating

The tablet cores of Example 4 were coated as described below. Table 8 shows the name of the various coats and their ingredients.

TABLE 8

| | Ingredients | Weight per batch* (kg) | Weight per tablet (mg) |
|---|---|---|---|
| | Diclectin 10 mg - uncoated cores (from Example 4 above) | 100 | 145.0 |
| | Clear Coat #1 and #2 | | |
| 1 | Sterile purified water | 74.1 | — |
| 2 | Opadry ™ Clear 02O190000 | 9.631 | 9.31 |
| | Enteric Coat | | |
| 3 | Sterile purified water | 61.6 | — |
| 4 | Simethicone Emulsion 30% USP, KH | 0.008 | 0.003 |
| 5 | Triethyl Citrate NF, K | 1.611 | 1.67 |
| 6 | Acryl-EZE ™ Clear | 13.819 | 14.31 |
| | Clear Coat with Pyridoxine HCl | | |
| 7 | Sterile purified water | 89.88 | — |
| 8 | Opadry ™ Clear 02O190000 | 9.356 | 9.04 |
| 9 | Pyridoxine HCl | 10.375 | 10.03 |
| | Clear Coat #3 | | |
| 10 | Sterile purified water | 45.2 | — |
| 11 | Opadry ™ Clear 02O190000 | 5.877 | 5.88 |
| | Clear Coat with Doxylamine Succinate | | |
| 12 | Sterile purified water | 114.9 | — |
| 13 | Opadry ™ Clear 02O190000 | 14.868 | 14.37 |
| 14 | Doxylamine succinate USP | 10.354 | 10.01 |
| | Pink Coat | | |
| 15 | Sterile purified water | 63.0 | — |
| 16 | Opadry ™ II Pink 85F94320 | 11.122 | 13.17 |
| | Waxing | | |
| 17 | Carnauba wax powder NF | 0.030 | .04 |
| | Total weight of coated tablets | | 232.6 |

*Batch size: 689 655 tablets

Table 9 shows the names and ingredients of the coating solutions and suspensions that were prepared for the coating process.

TABLE 9

| Solution/Suspension | Ingredients (no. from Table 8) |
| --- | --- |
| Clear Coating Solution #1 and #2 | 1 and 2 |
| Enteric Coating Suspension | 3, 4, 5, and 6 |
| Clear Coating Solution with Pyridoxine HCl | 7, 8, and 9 |
| Clear Coating Solution #3 | 10 and 11 |
| Clear Coating Solution with Doxylamine Succinate | 12, 13, and 14 |
| Pink Coating Suspension | 15 and 16 |

Table 10 shows the order in which the coats were applied on the tablet cores, the target weight gain for each coating step, and which coating solution/suspension was used to produce which coating. Coating was carried out using a 48 inches Accela Cota™ equipped with half-moon 4 inches shield and baffles.

TABLE 10

| Order | Coat | Solution/Suspension | Target weight gain (%) |
| --- | --- | --- | --- |
| 1 | Clear Coat #1 | Clear Coating Solution #1 and #2 | 3.0 |
| 2 | Enteric Coat | Enteric Coating Suspension | 10.7 |
| 3 | Clear Coat #2 | Clear Coating Solution #1 and #2 | 3.0 |
| 4 | Clear Coat with Pyridoxine HCl | Clear Coating Solution with Pyridoxine HCl | 11.2 |
| 5 | Clear Coat #3 | Clear Coating Solution #3 | 3.0 |
| 6 | Clear Coat with Doxylamine Succinate | Clear Coating Solution with Doxylamine Succinate | 12.5 |
| 7 | Pink Coat | Pink Coating Suspension | 6.0 |

Then, the tablets were waxed with ingredient no. 17 (carnauba wax powder) in a pan coater. The composition of the final product is presented in Table 11.

TABLE 11

| Ingredient | mg/tablet | % of final product |
| --- | --- | --- |
| Core | 145 | 62.3 |
| Microcrystalline cellulose | 90 | 38.7 |
| Doxylamine Succinate | 10 | 4.3 |
| Pyridoxine HCl | 10 | 4.3 |
| Colloidal Silicon Dioxide | 1 | 0.43 |
| Magnesium trisilicate | 26.4 | 11.3 |
| Croscarmellose sodium | 3.6 | 1.5 |
| Magnesium stearate | 4 | 1.7 |
| Clear seal coating 1 (Opacity ™ Clear) | 4.35 | 1.9 |
| Enteric coating | 15.98 | 6.9 |
| Simeticone | 0.003 | 0.0012 |
| Acryl-EZE ™ Clear | 14.31 | 6.2 |
| triethyl citrate | 1.67 | 0.7 |
| Clear seal coating 2 (Opadry ™ Clear) | 4.96 | 2.1 |
| API coating 1 | 19.07 | 8.2 |
| Clear coating (Opadry ™ Clear) | 9.04 | 3.9 |
| Pyridoxine HCl | 10.03 | 4.3 |
| Clear seal coating 3 (Opadry ™ Clear) | 5.68 | 2.4 |
| API coating 2 | 24.38 | 10.5 |
| Clear coating (Opadry ™ Clear) | 14.37 | 6.2 |
| Doxylamine succinate | 10.01 | 4.3 |
| Final pink coating | 13.17 | 5.7 |
| Wax | 0.04 | 0.017 |
| Final product | 232.6 | 100 |

Although the present invention has been described hereinabove by way of specific embodiments thereof, it can be modified, without departing from the nature of the subject invention as defined in the appended claims. The scope of the claims should not be limited by the preferred embodiments set forth in the examples, but should be given the broadest interpretation consistent with the description as a whole. In the claims, the word "comprising" is used as an open-ended term, substantially equivalent to the phrase "including, but not limited to". The singular forms "a", "an" and "the" include corresponding plural references unless the context clearly dictates otherwise.

The invention claimed is:

1. A solid oral dosage form comprising:
    (I) a delayed release component comprising:
        (a) a core comprising from about 5 mg to about 40 mg of doxylamine and/or a pharmaceutically acceptable salt thereof and from about 5 mg to about 40 mg of pyridoxine and/or a pharmaceutically acceptable salt thereof; and
        (b) an enteric coating surrounding said core; and
    (II) an immediate release component comprising:
        (c) a first active ingredient-containing immediate release coating surrounding said enteric coating and comprising (i) from about 5 mg to about 40 mg of doxylamine and/or a pharmaceutically acceptable salt thereof, or (ii) from about 5 mg to about 40 mg of pyridoxine and/or a pharmaceutically acceptable salt thereof; and
        (d) a second active ingredient-containing immediate release coating surrounding said first active ingredient-containing coating and comprising (i) from about 5 mg to about 40 mg of doxylamine and/or a pharmaceutically acceptable salt thereof, or (ii) from about 5 mg to about 40 mg of pyridoxine and/or a pharmaceutically acceptable salt thereof;
wherein if said first active ingredient-containing immediate release coating comprises said doxylamine and/or pharmaceutically acceptable salt thereof, said second active ingredient-containing immediate release coating comprises said pyridoxine and/or pharmaceutically acceptable salt thereof, and if said first active ingredient-containing immediate release coating comprises said pyridoxine and/or pharmaceutically acceptable salt thereof, said second active ingredient-containing immediate release coating comprises said doxylamine and/or pharmaceutically acceptable salt thereof.

2. The solid oral dosage form of claim 1, wherein said core comprises about 10 mg of said doxylamine or pharmaceutically acceptable salt thereof.

3. The solid oral dosage form of claim 1, wherein said core comprises doxylamine succinate.

4. The solid oral dosage form of claim 1, wherein said core comprises about 10 mg of said pyridoxine or pharmaceutically acceptable salt thereof.

5. The solid oral dosage form of claim 1, wherein said core comprises pyridoxine hydrochloride.

6. The solid oral dosage form of claim 1, wherein said first or second active ingredient-containing immediate release coating comprises about 10 mg of said doxylamine or pharmaceutically acceptable salt thereof.

7. The solid oral dosage form of claim 1, wherein said first or second active ingredient-containing immediate release coating comprises doxylamine succinate.

8. The solid oral dosage form of claim 1, wherein said first or second active ingredient-containing immediate release coating comprises about 10 mg of said pyridoxine or pharmaceutically acceptable salt thereof.

9. The solid oral dosage form of claim 1, wherein said first or second active ingredient-containing immediate release coating comprises pyridoxine hydrochloride.

10. The solid oral dosage form of claim 1, wherein said first and/or second active ingredient-containing immediate release coating comprises an immediate release film coating system.

11. The solid oral dosage form of claim 1, wherein said core is present in an amount of about 50% to about 70% (w/w) of said solid oral dosage form.

12. The solid oral dosage form of claim 1, wherein said enteric coating is present in an amount of about 2% to about 15% (w/w) of said solid oral dosage form.

13. The solid oral dosage form of claim 1, wherein said enteric coating comprises an acrylic polymer or co-polymer.

14. The solid oral dosage form of claim 13, wherein said acrylic polymer or co-polymer is a copolymer based on methacrylic acid and ethyl acrylate.

15. The solid oral dosage form of claim 1, wherein said first active ingredient-containing immediate release coating is present in an amount of about 4% to about 12% (w/w) in said solid oral dosage form.

16. The solid oral dosage form of claim 1, further comprising a first intermediate coating surrounding said first active ingredient-containing immediate release coating.

17. The solid oral dosage form of claim 16, wherein said first intermediate coating is present in an amount of about 1% to about 4% (w/w) in said solid oral dosage form.

18. The solid oral dosage form of claim 16, wherein said first intermediate coating comprises a film coating system.

19. The solid oral dosage form of claim 1, wherein said second active ingredient-containing immediate release coating is present in an amount of about 5% to about 15% (w/w) of said solid oral dosage form.

20. The solid oral dosage form of claim 1, further comprising a second intermediate coating between said core and said enteric coating.

21. The solid oral dosage form of claim 1, further comprising a third intermediate coating between said enteric coating and said first active ingredient-containing immediate release coating.

22. The solid oral dosage form of claim 1, further comprising a seal coating surrounding said second active ingredient-containing immediate release coating.

23. The solid oral dosage form of claim 22, wherein said seal coating is present in an amount of about 2% to about 10% (w/w) of said solid oral dosage form.

24. The solid oral dosage form of claim 22, wherein said seal coating comprises a film coating system.

25. The solid oral dosage form of claim 22, further comprising a solid oral dosage form-coating agent surrounding said seal coating.

26. The solid oral dosage form of claim 25, wherein said solid oral dosage form-coating agent is present in an amount of about 0.005% to about 0.5% (w/w) of said solid oral dosage form.

27. The solid oral dosage form of claim 25, wherein said solid oral dosage form-coating agent comprises wax.

28. The solid oral dosage form of claim 1, wherein said solid oral dosage form is a tablet.

29. A solid oral dosage form comprising:
(I) a delayed release component comprising:
 (a) a core comprising about 10 mg of doxylamine succinate and about 10 mg of pyridoxine hydrochloride;
 (b) a second intermediate coating surrounding said core;
 (c) an enteric coating surrounding said second intermediate coating; and
 (d) a third intermediate coating surrounding said enteric coating; and
(II) an immediate release component comprising:
 (e) a first active ingredient-containing immediate release coating surrounding said third intermediate coating and comprising about 10 mg of pyridoxine hydrochloride;
 (f) a first intermediate coating surrounding said first active ingredient-containing immediate release coating;
 (g) a second active ingredient-containing immediate release coating surrounding said first intermediate coating and comprising about 10 mg of doxylamine succinate;
 (h) a seal coating surrounding said second active ingredient-containing immediate release coating; and
 (i) a solid oral dosage form-coating agent surrounding said seal coating.

30. A method for alleviating the symptoms of nausea and vomiting of human pregnancy, said method comprising administering the solid oral dosage form of claim 1 to a pregnant human female in need thereof.

* * * * *